(12) United States Patent  
Goldenberg

(10) Patent No.: US 7,278,970 B2  
(45) Date of Patent: Oct. 9, 2007

(54) BIOPSY NEEDLES

(76) Inventor: Alec S. Goldenberg, 157 E. 32nd St., Second Floor, New York, NY (US) 10016

( * ) Notice: Subject to any disclaimer, the term of this patent is extended or adjusted under 35 U.S.C. 154(b) by 518 days.

(21) Appl. No.: 10/901,917

(22) Filed: Jul. 29, 2004

(65) Prior Publication Data

US 2005/0054948 A1  Mar. 10, 2005

Related U.S. Application Data

(60) Provisional application No. 60/500,536, filed on Sep. 4, 2003, provisional application No. 60/491,163, filed on Jul. 29, 2003.

(51) Int. Cl.  
*A61B 10/00* (2006.01)
(52) U.S. Cl. .................................... 600/564
(58) Field of Classification Search ........ 600/562–568, 600/3  
See application file for complete search history.

(56) References Cited

U.S. PATENT DOCUMENTS

| 5,634,473 A | * | 6/1997 | Goldenberg et al. | ........ 600/567 |
| 6,063,037 A | * | 5/2000 | Mittermeier et al. | ........ 600/567 |
| 7,041,047 B2 | * | 5/2006 | Gellman et al. | ............... 600/3 |

* cited by examiner

*Primary Examiner*—Max Hindenburg  
*Assistant Examiner*—Brian Szmal  
(74) *Attorney, Agent, or Firm*—Darby & Darby

(57) ABSTRACT

In one embodiment, a biopsy needle that is particularly suited for shearing and collecting soft tissue specimens is provided and is formed of an inner tube with a snare at a distal end thereof, an outer cannula, a stylet and a handle assembly. The handle assembly includes a spring loaded mechanism that permits the user to selectively actuate the biopsy needle so that the outer cannula and the inner tube are rapidly advanced beyond the stylet to provide a shearing action of the soft tissue specimen.

37 Claims, 9 Drawing Sheets

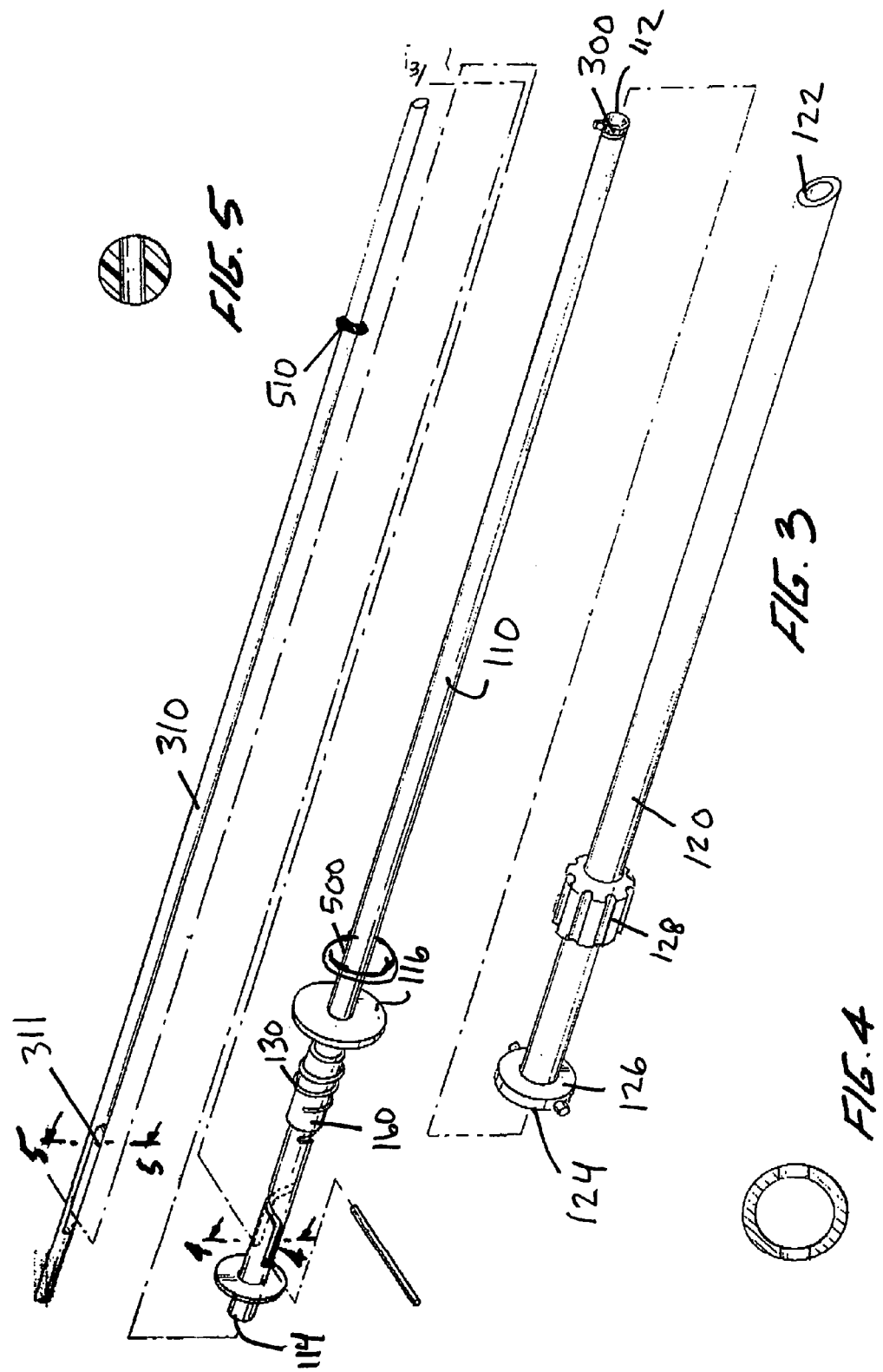

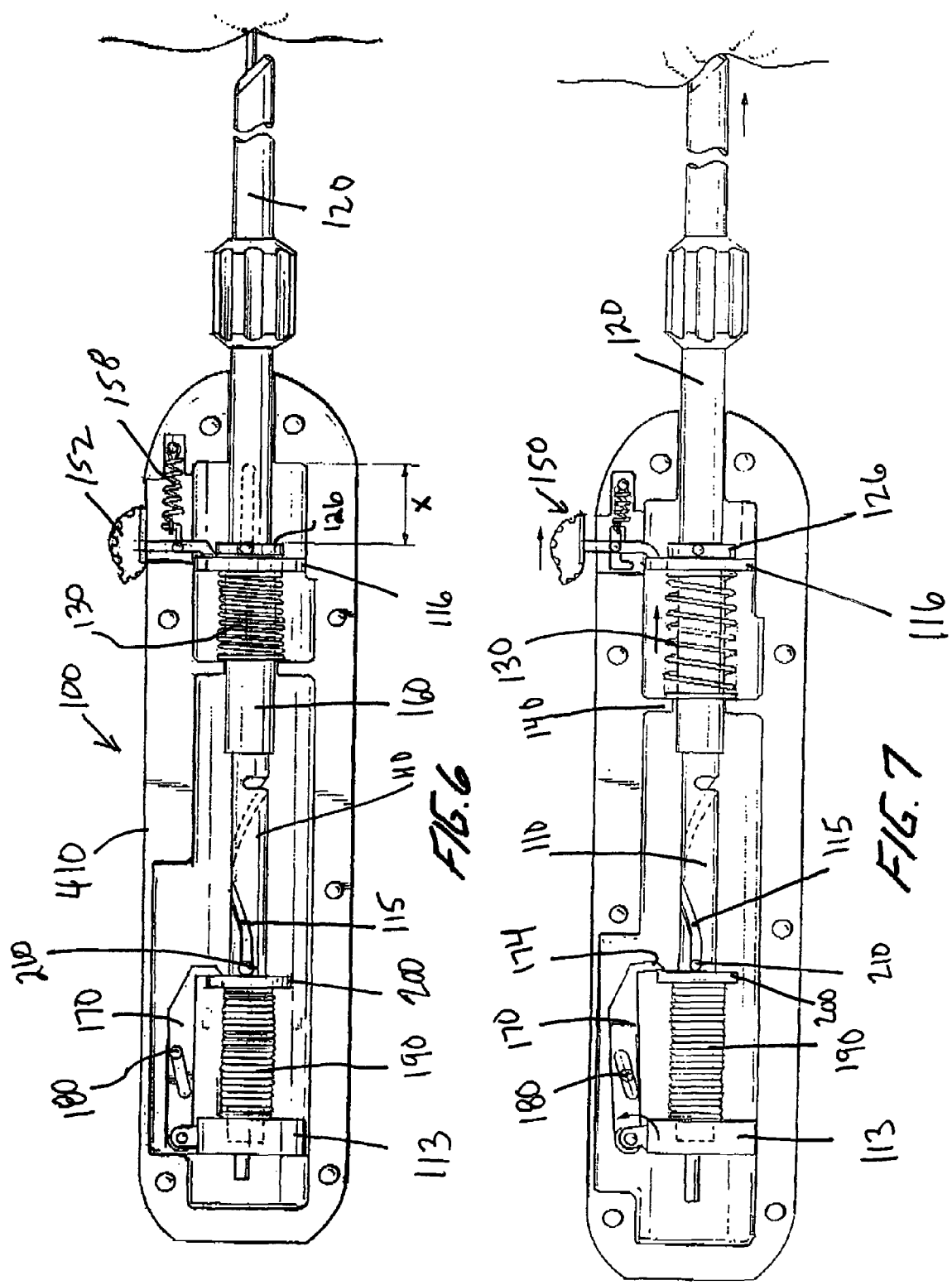

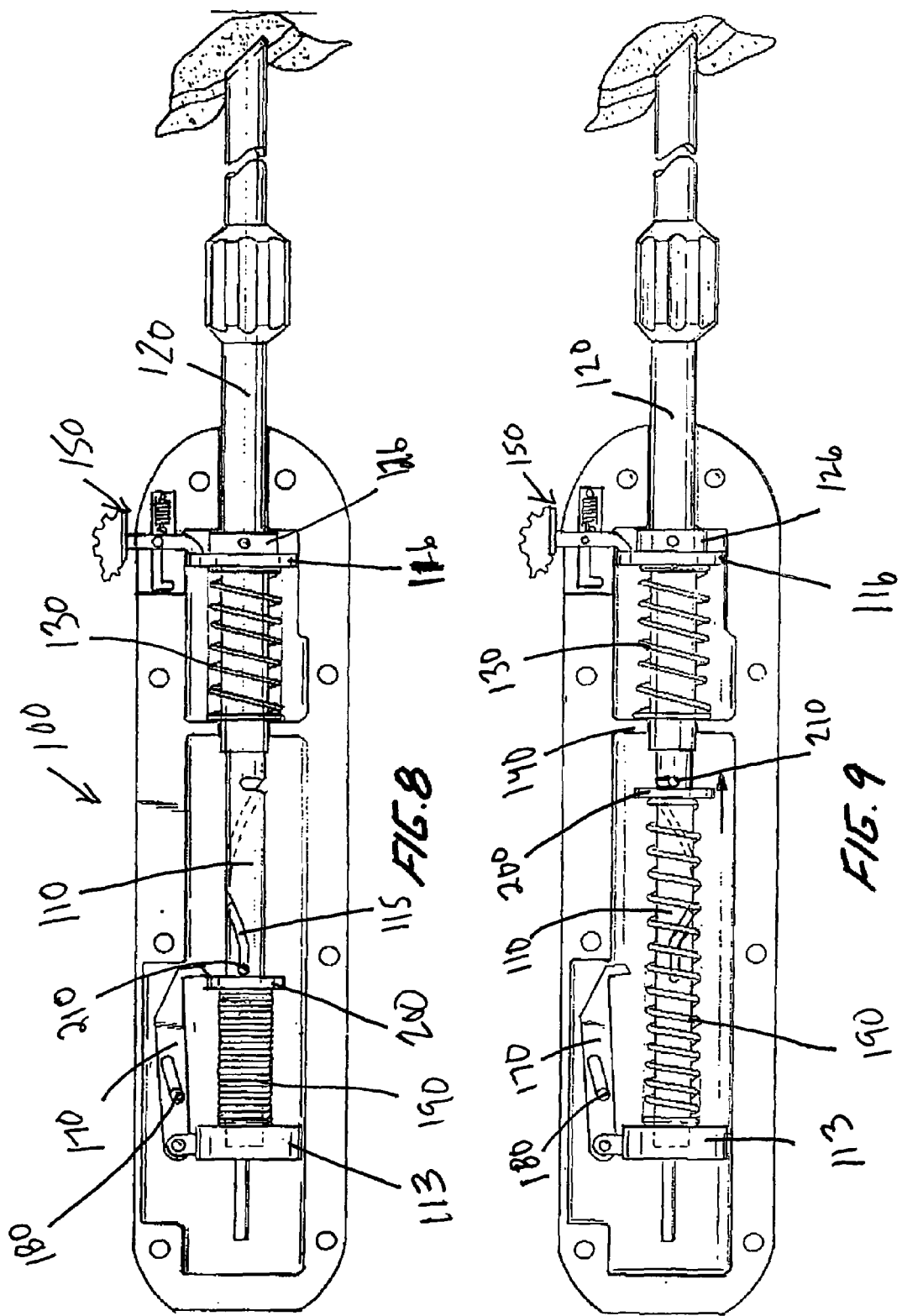

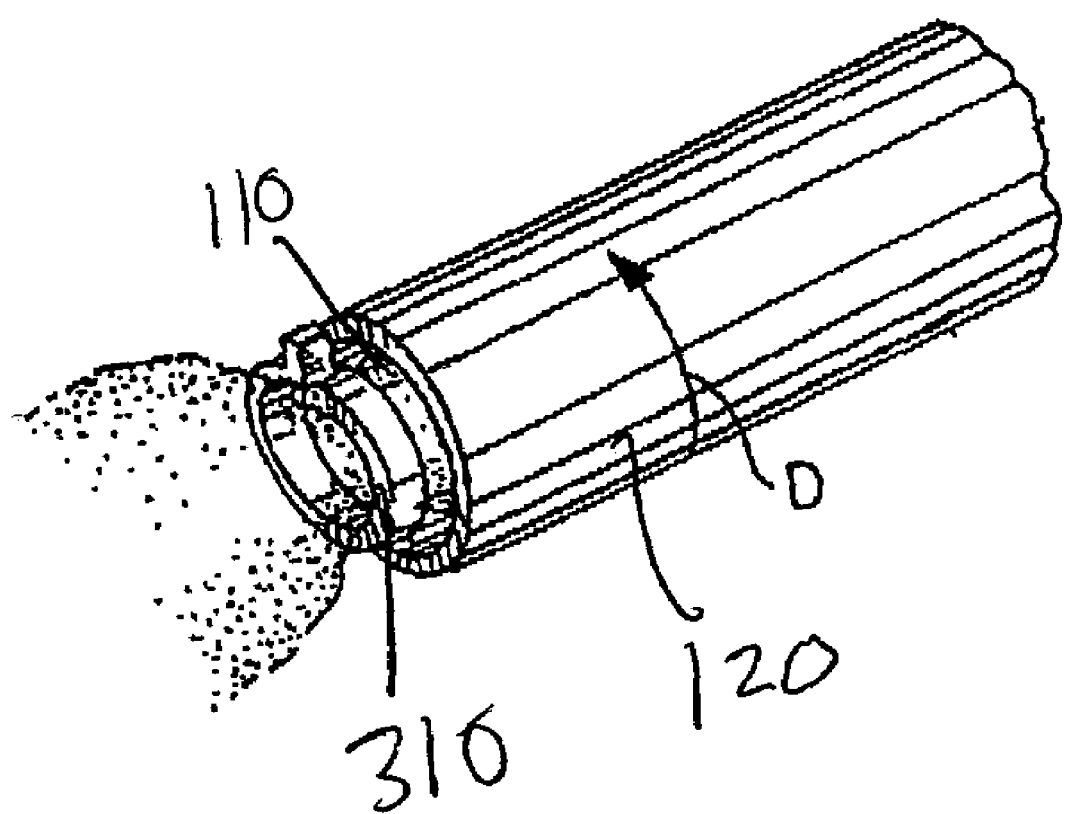

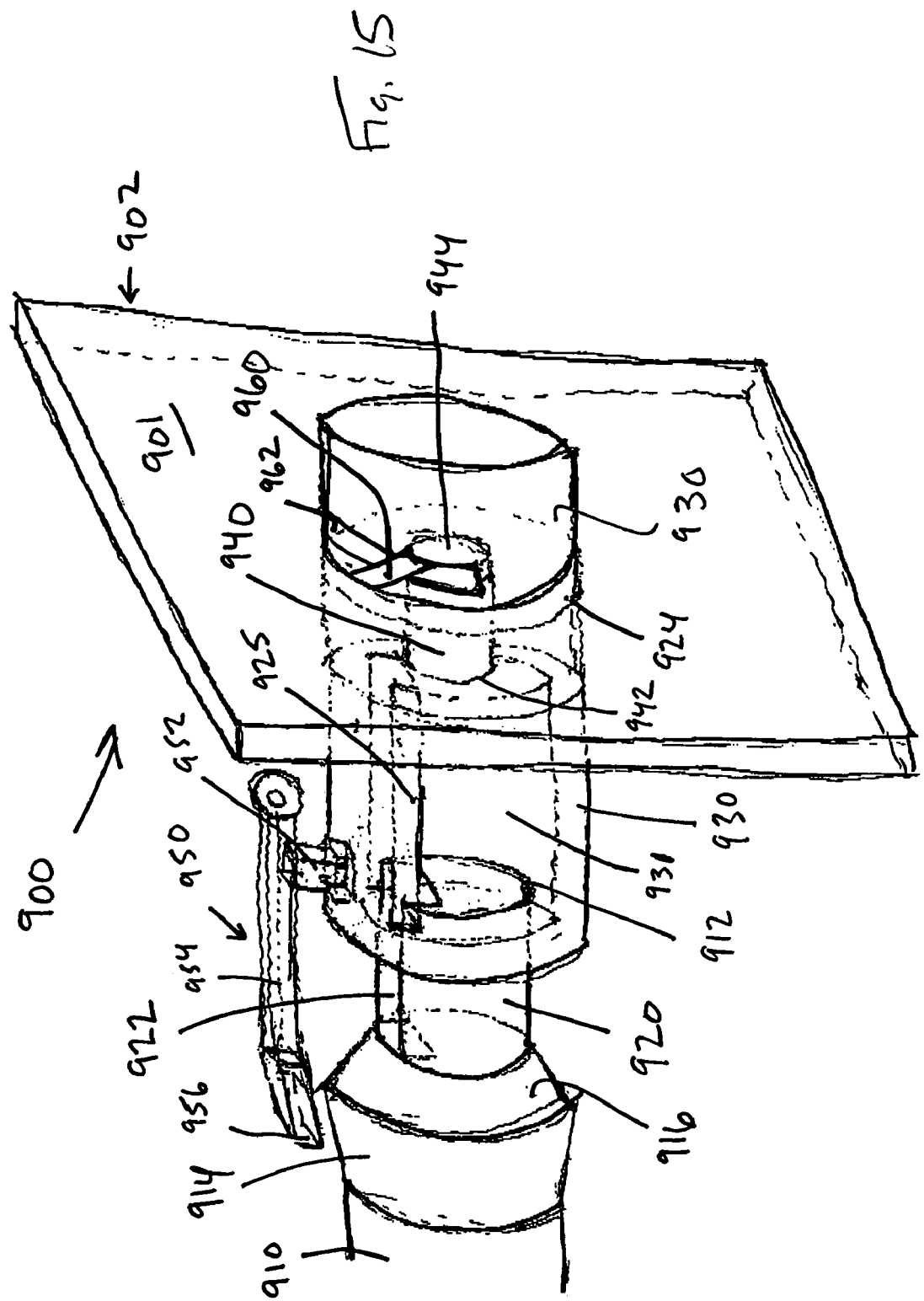

BIOPSY NEEDLES

CROSS-REFERENCE TO RELATED APPLICATIONS

The present application claims the benefit of U.S. patent application Ser. No. 60/491,163, filed Jul. 29, 2003 and U.S. patent application Ser. No. 60/500,536, filed Sep. 4, 2003, both of which are hereby incorporated by reference in their entirety.

TECHNICAL FIELD

The present invention relates to a surgical instrument, typically known as a biopsy needle or cannula that is used to gather tissue from living persons or animals for pathological study and more particularly, relates to a biopsy needle having an improved structure for severing a soft tissue sample and/or retaining the tissue sample within the biopsy needle.

BACKGROUND

For various medical reasons, such as diagnostic tests or the like, it is often necessary for a physician to obtain a sample of a patient's body. Often, it is required to take a sample from a non-bony organ or tissue, or soft tissue rather than from a more rigid structure, such as a bone or bone marrow specimen. Soft tissue specimens by definition generally contain a less rigid structure and are compared with bone or bone marrow structures which are recovered with significant portions of their internal bony structure intact.

One exemplary surgical instrument for the severing and/or retrieval of tissue is disclosed in U.S. Pat. Nos. 5,522,398; 5843,001; and 6,015,391, of which the present applicant is also inventor. While these instruments are particularly suited for severing and collecting a more rigid tissue specimen, such as a bone marrow specimen, the instruments are not as effective at severing and/or retaining soft tissue samples. Also, the recovery of a soft tissue specimen by pushing it back through the handle from the tip of the needle may not be as the applicable for these specimens as it is for bone marrow specimens with preserved internal structure. An attempt to push the specimen through the needle could result in disruption of a specimen because a soft tissue specimens has less structure. Moreover in a long needle, such as an endoscopic SNARECOIL (trademark) needle, the length of the needle would be prohibitive in attempting to recover a specimen by pushing it out of the proximal end of the needle.

Other conventional procedures and instruments used for obtaining the samples, while not overly complex, almost universally result in excessive patient discomfort and often overly extends the patient's and operator's time and money.

SUMMARY

In one embodiment, a biopsy needle for collecting a tissue specimen is provided and includes an inner tube with a snarecoil operatively connected at a distal end thereof, an outer cannula, a stylet and a handle assembly. The handle assembly includes an actuatable drive mechanism for rapidly driving the inner tube and the outer cannula, in an axial direction, over the stylet to a position where the inner tube and the outer cannula are advanced beyond a distal end of the stylet to provide a shearing action of the tissue specimen. The needle also includes a torque generating mechanism associated with at least the inner tube that is actuatable to translate a torque to the inner tube relative to the outer cannula. This applied torque results in rotation of the inner tube and this results in activation of a winding down of the snarecoil. Preferably, the actuation of both the drive mechanism and the torque generating mechanism are coordinated with one another.

There are a great number of different embodiments that can incorporate one or more of the above features, with the below descriptions being merely one or more suitable embodiments for a needle within the spirit of the present invention.

In one embodiment, a biopsy needle that is particularly suited for shearing and collecting soft tissue specimens is provided and is formed of an inner tube with a snare at a distal end thereof, an outer cannula, a stylet and a handle assembly. In one aspect of the present invention, the handle assembly includes a spring loaded mechanism described in greater detail below that permits the user to selectively actuate the biopsy needle so that the outer cannula and the inner tube are rapidly advanced beyond the stylet to provide a shearing action of the soft tissue specimen.

In another aspect of the present invention and according to one exemplary embodiment, the rapid advancement of the needle to achieve appropriate shear/cutting forces and to facilitate specimen transit into the needle is accomplished by the spring loaded mechanism in which there is coordination between the rapid advancement of the needle over the shaft and activation of the winding down of the snarecoil. This can be accomplished using a spring-loaded mechanism to achieve the forward energy of needle projection and snare activation by means of a pin and profiled groove (slot) arrangement where the pin travels with the profiled groove as the needle is fired over the stylet and this in turn is translated into rotation of the inner tube when the pin is rapidly advanced forward using another spring-loaded arrangement, which causes the snare to at least partially close. As used herein, the term "groove" can refer to both a recessed channel formed in a body or a slot (opening) formed completely through the body.

In these embodiments, the pin and groove move relative to each other and this can be achieved by either translating a grooved sleeve axially relative to a pin that does not move axially or vice versa translating the pin relative to a grooved sleeve that does not move in an axial position. In each of these configurations, one component (either the grooved sleeve or pin) does not rotate, while the other component does rotate and is attached to the inner tube. The pin engages the groove by projecting into the groove or complementary helical grooves in a radial fashion. In other embodiments the inner Snarecoil tube can be axially translated relative to the outer tube causing the Snarecoil to change its geometry and facilitate specimen capture. Axial translation of a pin or groove attached to the inner tube relative to a fixed groove or pin, respectively will also cause the inner tube to rotate resulting in a decrease in the Snarecoil diameter. In one embodiment, if the pin is fixed and does not rotate, axial movement of the sleeve causes the sleeve and any tube attached thereto (e.g., inner tube attached to snarecoil) to rotate.

In another aspect, a negative pressure internal to the needle is generated by taking advantage of the concept that when the needle is "thrown" forward over the stylet, the stylet is moving backward relative to the needle. As a result, the incorporation of a seal, such as a rubber O-ring or the like, between the stylet and the inner tube can generate a small but significant vacuum internal to the distal portion of the needle facilitating specimen transit into the needle. The vacuum is thus generated when the needle is "thrown" over the stylet and is cutting the tissue. The seal facilitates the stylet acting as a piston that generates an internal negative pressure in the needle, e.g., within the inner needle, to help draw the specimen by negative pressure into the inner tube. In another embodiment a seal is incorporated between a stylet and a single tube needle resulting in a negative pressure internal to the needle as it is rapidly projected forward over the stylet.

In another aspect, the inner tube and outer cannula each has a slot formed therethrough which provides access to the respective interior of each member. When the two slots are aligned as by rotating the inner tube relative to the outer cannula, a window is opened and permits the user to access the interior of the inner tube from outside the outer cannula by inserting an instrument through the side window into the interior of the inner tube to access the specimen so that it can be removed through the window.

Other features and advantages of the present invention will be apparent from the following detailed description when read in conjunction with the accompanying drawings.

BRIEF DESCRIPTION OF THE DRAWING FIGURES

The foregoing and other features of the present invention will be more readily apparent from the following detailed description and drawings figures of illustrative embodiments of the invention in which:

FIG. 3 is an exploded perspective view of an inner tube, outer cannula, and stylet that are part of the needle of FIG. 1;

FIG. 4 is a cross-sectional view taken along the line 4-4 of FIG. 3;

FIG. 5 is a cross-sectional view taken along the line 5-5 of FIG. 3;

FIG. 6 is a cross-sectional elevation view of the needle of FIG. 1 in a rest position;

FIG. 7 is a cross-sectional elevation view of the needle of FIG. 1 at an intermediate position of a first stage;

FIG. 8 is a cross-sectional elevation view of the needle of FIG. 1 shown at the completion of the first stage;

FIG. 9 is a cross-sectional elevation view of the needle of FIG. 1 shown at the completion of the second stage;

FIG. 10 is a sectional view of the snare after it has been activated;

FIG. 15 is a perspective partial view of a torque generating mechanism according to another embodiment for selectively generating torque in a member.

DETAILED DESCRIPTION OF PREFERRED EMBODIMENTS

Figure 1:
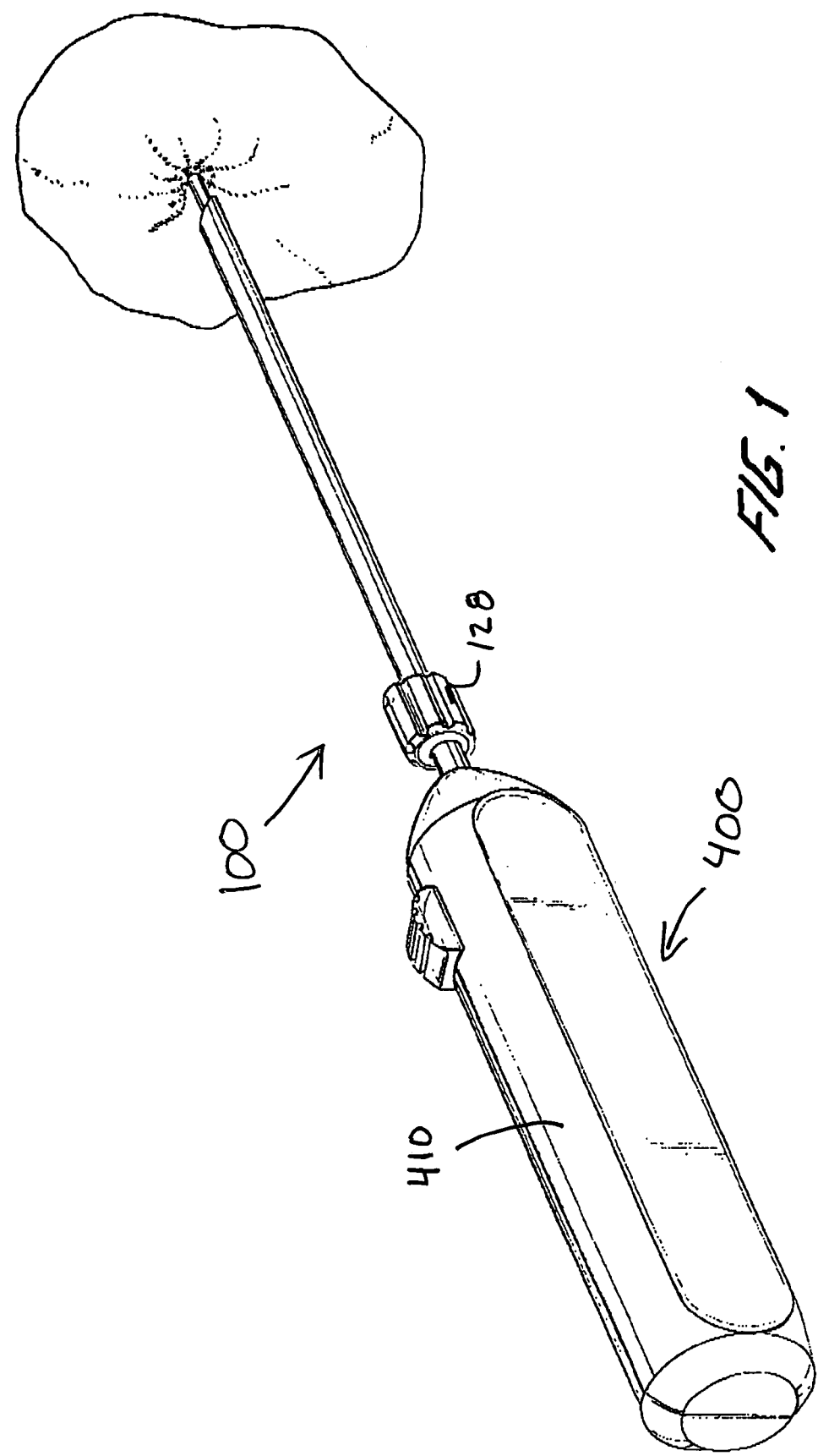
FIG. 1 is a perspective view of a biopsy needle according to a first embodiment shown in relation to a tissue site.
Figure 2:
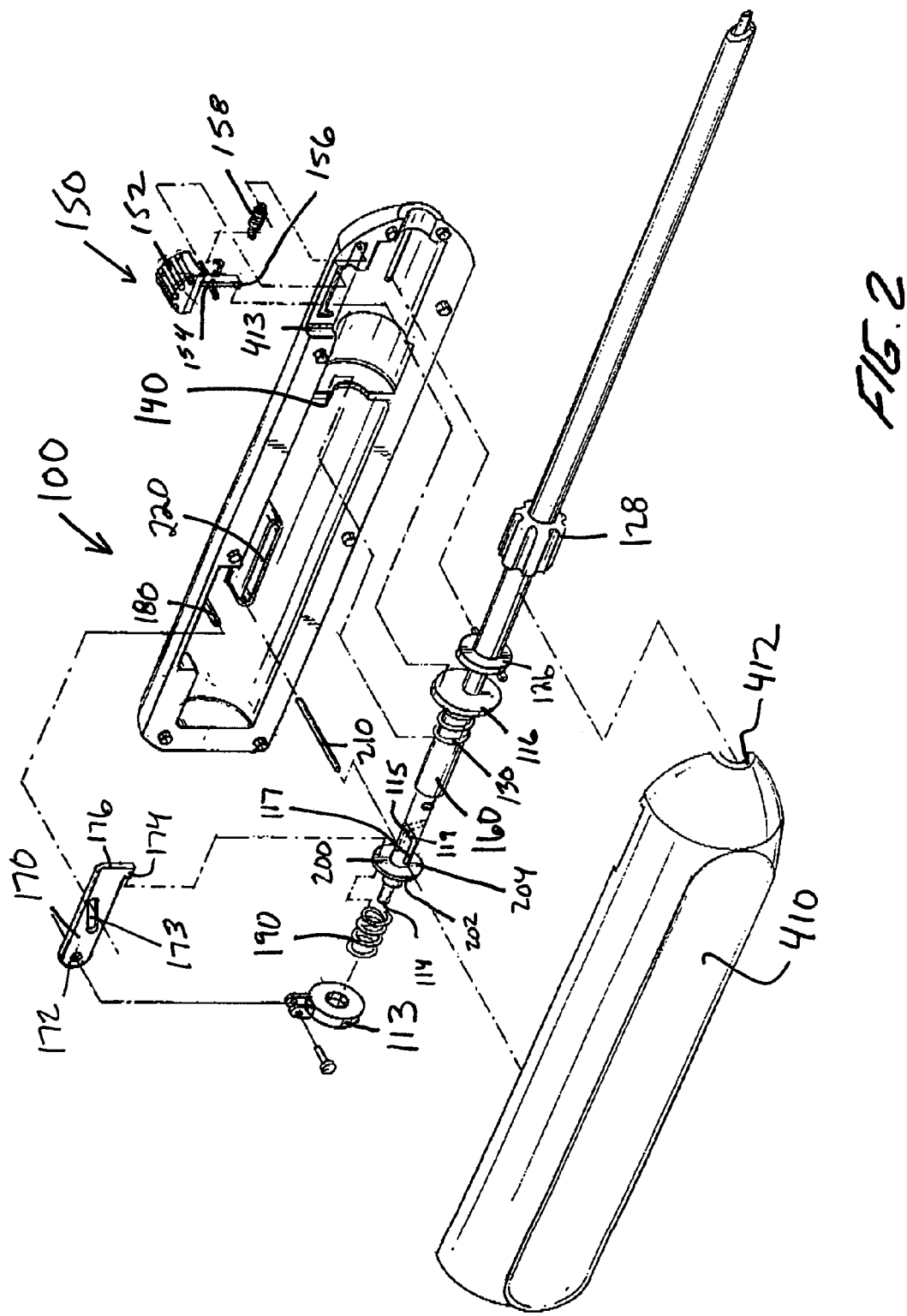
FIG. 2 is an exploded perspective of the biopsy needle of FIG. 1.

Referring now to FIGS. 1-5, a biopsy needle 100 according to one exemplary embodiment is illustrated. The biopsy needle 100 includes an inner tube 110 with a snare (Snare-coil) 300 at a distal end 111 thereof, an outer cannula 120, a stylet 310 and a handle assembly 400. In one aspect of the present invention, the handle assembly 400 includes a spring loaded mechanism described in greater detail below that permits the user to selectively actuate the biopsy needle 100 so that the outer cannula 120 and the inner tube 110 are rapidly advanced beyond the stylet 310 to provide a shearing action of the soft tissue specimen.

The present biopsy needle 100 is constructed for soft biopsy applications since the spring loaded mechanism provides an improved means of removing the tissue after it is cored as wells as providing an improvement in the way that the tissue is acquired by the needle 100. The handle assembly 400 includes a handle body 410 that can be formed in a number of different shapes and sizes and is generally a hollow body that contains the spring loaded mechanism. For purpose of illustration only, the handle body 410 of FIG. 1 is a generally rectangular or square body; however, handle body 410 preferably is an ergonomically pleasing shape. The handle body 410 includes an opening 412 that permits a portion of a first mechanical mechanism to extend therethrough so as to be accessible by the user as is described in greater detail below.

The inner tube 110 is preferably similar or identical to the inner tube disclosed in one of the aforementioned patents. More specifically, the inner tube 110 includes a distal end 112 and an opposing proximal end 114. The inner tube 110 can have any number of different cross-sectional shapes; however, in one embodiment, the inner tube 110 has a circular cross-section. Near the proximate end 114, the inner tube 110 includes a flange 116 that extends outwardly from the inner tube 110. The flange 116 can be in the form of an annular flange that extends completely around the inner tube 110 or it can be in the form of one or more protrusions, e.g., tabs, that extend outward from the inner tube 110. In the illustration embodiment, the flange 116 is in the form of an annular ring.

The outer cannula 120 is preferably similar or identical to the outer tube disclosed in one of the aforementioned patents. More specifically, the outer cannula 120 includes a distal end 122 and an opposing proximal end 124. The outer cannula 120 can also have any number of different cross-sectional shapes with one embodiment being a circular tube structure. At the proximal end 124 of the outer cannula 120, a flange 126 is formed. As with the flange 116, the flange 126 can be in the form of an annular flange or it can be formed by one or more protrusions or tabs. The outer cannula 120 also has a stop 128 formed as a part thereof near the proximal end 124. The stop 128 provides a means for the user to reset the entire spring loaded mechanism after the user has activated (fired) it and the inner tube 110 and outer cannula 120 have advanced. The stop 128 is designed as a member that the user can apply a force to in a direction toward the handle body 410 so as to reset the inner tube 110 and outer cannula 120 by retracting them back into the handle body 410. The stop 128 can be in the form of an annular flange, similar to the other flanges, or it can be one or more tabs that extend away from the outer cannula 120 to provide a member that the user can press against to directly retract the outer cannula 120, as well as the joined inner tube 110, back into the handle body 410. In the illustrated embodiment, the stop 128 is in the form of an annular flange that extends completely around the outer cannula 120. The stop 128 is always disposed outside of the handle body 410 since the opening 412 that is formed in the handle body 410 is sized relative to the outer diameter of the outer cannula 120 so that the outer cannula 120 (and the inner tube 110 and stylet 310 disposed inside the outer cannula 120) is movably disposed through the opening 412 but the stop 128 can not travel through the opening 412. Thus, when the user presses against the stop 128, the degree of travel of the outer cannula 120 is limited due to the presence of the stop 128, see FIG. 9. In other words, a pressing action by the user on the stop 128 causes the spring loaded mechanism to reset itself. Since the inner tube 110 is connected to the outer cannula 120 at their distal ends 112, 122, the axial movement of the outer cannula 120 is directly translated into axial movement of the inner tube 110 due to a force exerted by the flange 126 (outer cannula 120) onto the flange 116 (inner tube 110).

Before proceeding to an explanation of the other operable components of the spring loaded mechanism, it is helpful to understand that generally the inner tube 110 and outer cannula 120 are positionable between two positions, namely, a fully retracted position and a fully extended position. In the fully retracted position, the inner tube 110 and outer cannula 120 are reset back into the handle body 410 and a biasing element(s) of the spring loaded mechanism stores energy. In contrast, after the user activates the spring loaded mechanism, the biasing element releases its energy and an axial force is applied to the inner and outer tube structure in a direction away from the handle body 410.

In both the fully retracted and fully extended positions, the flange members 116, 126 contact or seat against one another so that a force applied to one of the inner tube 110 and the outer cannula 120 is translated to the other of the inner tube 110 and outer cannula 120.

In order to generate a force that is sufficient to shear the soft tissue, the spring loaded mechanism includes a first biasing element 130, such as a coil spring, that applies a force against a face of the annular flange 116 that is opposite the face that seats against the annular flange 126 of the outer cannula 120. The first biasing element 130 is contained within the handle body 410 by being disposed between the annular flange 116 and an interference member 140 that is formed as part of the handle body 410 such that the inner tube 110 can freely travel therethrough in a sliding manner, while the first biasing element 130 is external to the inner tube 110. More specifically, the interference member 140 can be in the form of an annular flange that has an opening formed therethrough to accommodate the outer cannula 120. The annular flange 140 is thus fixed relative to the handle 400 and relative to the movable inner tube 110 and outer cannula 120. The first biasing element 130 surrounds the inner tube 110 and between the annular flanges 116 and 140 and when the inner tube/outer cannula 110, 120 are moved toward the handle body 410, the first biasing element 130 is placed under compression since the distance between the flanges 116, 140 is decreased, thereby constraining the first biasing element 130 in a smaller space. It will be understood that the annular flange 140 does not necessarily have to completely surround the inner tube 110 but rather, the annular flange 140 can be formed of two or more tabs on which one end of the first biasing element 130 sits.

The spring loaded mechanism includes an operable actuator device 150 that causes the release of the first biasing element 130 from its compressed state, thereby resulting in the first biasing element 130 releasing at least some of its stored energy. One exemplary actuator device 150 is a pivotable lever that at least partially extends through an opening 413 formed in the handle body 410. The device 150 has a button or the like 152 which the user manipulates to cause the pivoting of the device 150 and release of the first biasing element 130. The button 152 is disposed along an outer surface of the handle body 410. The device 150 is formed of an elongated finger or post 154 that has the button 152 attached or formed at one end and terminates at the other end in a claw or tab 15 that is provided to engage the annular flange 116 and lock the inner and outer tubes 110, 120 in the retracted position. The device 150 includes a biasing element, such as a spring, 158 that is attached at one end to the housing and at its other end to the post 154 which applies a biasing force to the post 154, thereby biasing the post 154 in a manner such that it engages and applies a force against the flange 116 when the device 150 is in a closed position. As the user slides the button 152, the biasing force of the spring 158 is overcome and the device 150 pivots about the post 154 in a direction where the claw 156 clears the flange 116, thereby releasing the inner tube 110 for axial movement.

In the illustrated embodiment, the first surface 161 and the outer face of the annular flange 116 are parallel to one another and in contact with one another. As previously mentioned, the first biasing element 130 applies a biasing force against the inner face of the annular flange 116, which in turn applies a force against the annular flange 126 of the outer cannula 120 since the flanges 116, 126 are in intimate contact with one another. When the surface of the claw 156 seats against the annular flange 116 it acts to lock the inner and outer tubes 110, 120 in the retracted position since it prevents any axial movement of the inner tube 110 in a direction away from the handle body 410.

As soon as the claw 156 becomes disengaged from the flange 116, the first biasing element 130 releases its stored energy by applying a force against the flange 116. This release of energy results in axial movement of the inner tube 110 and since the flange 116 contacts the end flange 126 of the outer cannula 120, the outer cannula 120 moves axially with the inner tube 110 as sequentially shown in FIGS. 6-8. The flange 126, as well as the flange 116, limits the degree of travel of the inner tube 110 and outer cannula 120 since the flanges 116, 126 have dimensions greater than the dimensions of the opening in the handle body 410 through which the outer cannula 120 extends. In the fully extended position, the flange 126 seats against the handle body 410 with the first biasing element 130 being in a more elongated condition between the stop 128 and the flange 116.

Preferably, a sleeve 160 is provided and is disposed around a portion of the inner tube 110. More specifically, one end of the sleeve 160 is disposed against the inner face of the flange 116 and the other end of the sleeve 160 terminates prior to the end 114 of the inner tube 110. It will be appreciated that the sleeve 160 extends to the flange 116 and that the first biasing element 130 is disposed around the sleeve 160 since the sleeve 160 is present in the location where the first biasing element 130 is located both when it is in a compressed state and a relaxed state. One exemplary sleeve 160 is thus a tubular structure that is complementary to the shape and size of the inner tube 110. The first biasing element 130 is disposed around the sleeve 160 with the sleeve 160 being received through the opening in the interference member 140 in a sliding manner.

The spring loaded mechanism has another component thereof in that it generally includes a pin and groove arrangement to control the specific movements of the inner tube 110 as it is fired and advanced away from the handle body 410 upon actuation of the spring loaded mechanism.

For example, the end 114 of the inner tube 110 has a flange member 113 which can be an annular flange or can be less than an annular flange. The end 114 (flange 113 thereof) thus has an opening formed thereat to permit the stylet 310 to be received and removed therethrough.

It will be appreciated that the inner tube 110 should be able to rotate within the flange 113 and therefore, it is preferred that the flange 113 be connected to the inner tube 110 in a non-movable manner so as to permit the inner tube 110 to rotate when it is axially advances as will be described hereinafter. For example and as shown in FIG. 6, first and second locator members 177, 179 are disposed around the flange 113 so as to locate the flange 113 and limit the movement thereof. More specifically, the first locator member 177 is in the form of a distal flange (e.g., ring shaped) and the second locator member 179 (e.g., ring shaped) is in the form of a proximal flange. These flanges 177, 179 prevents flange 113 from translating along an axial (longitudinal) direction relative to the inner tube 110 but allows the inner tube 110 to freely rotate within the flange 113.

As described in detail below, the inner tube 110 is preferably operatively coupled to a torque generating mechanism that serves to impart a torque (rotation) to the inner tube 110. This rotation is desirable since it will cause activation of the snarecoil and capture of the tissue specimen. Thus, as used herein, the term torque generating mechanism refers to any type of mechanism, whether it be manually or automatically actuated, that translates a torque to the inner tube 110 so as to cause activation of the snarecoil and capture of the tissue specimen due to winding down of the snarecoil. In the embodiment where the torque generating mechanism is automatically actuated, the mechanism can also be referred to as an automatic active capture mechanism. In an embodiment where the needle does not include a snarecoil, the torque generating mechanism simply rotates the inner tube as opposed to actuating a snarecoil.

The illustrated torque generating mechanism includes a second pivotable lever 170 is provided and is pivotally connected to the flange 113 formed at the end of the inner tube 110. The lever 170 is preferably pivotally connected to the flange 113 at a first end 172 and has a claw or lip 174 formed at an opposing second end 176. The illustrated claw 174 is a protrusion that is generally perpendicular to the elongated body portion of the lever 170. The lever 170 includes an opening 173 formed therethrough to receive a pin or the like 180. In one aspect of the illustrated spring loaded mechanism, the opening 173 is a slot that is formed at an angle within the lever body and more specifically, the slot 173 is angled upward in a direction toward the claw 174. In the retracted, locked position of the spring loaded mechanism, the pin 180 is disposed within the slot 173 near or at the end that is closest to the claw 174, as shown in FIG. 6, and after activation of the first lever mechanism (actuator device 150), the pin 180 rides within the slot 173 toward the opposite end thereof causing the disengagement of the second pivotable lever 170 as will be described in greater detail hereinafter and as sequentially shown in FIGS. 6-9.

The illustrated pin and groove mechanism includes a second biasing element 190 that is disposed between the flange 113 and a movable member 200 that is disposed around the inner tube 110. The member 200 is free to slidably travel along the inner tube 110 when it is unlocked from the claw 174 of the lever 170. The member 200 thus has an opening extending therethrough that accommodates the inner tube 110 and has a first face 202 that faces and is in contact with the second biasing element 190 and a second face 204 that faces the sleeve 160/interference member 140.

In one exemplary embodiment, the member 200 is generally in the form of a ring shaped member. The member 200 has a surface that can be engaged by the claw 174 so as to keep the second lever mechanism in a locked position. In the locked position, the second biasing element 190 is in a compressed state (storing energy) between the first face 202 and the distal locator member 177 that is adjacent the flange 113 (as shown in FIG. 6).

According to the illustrated embodiment, the pin and groove mechanism is formed of a pin 210 and the inner tube 110 has a one or more profiled grooves 115 formed therein. In the illustrated embodiment, each groove 115 has a first generally linear portion 117 and a second portion 119 that is generally helical in nature.

The pin 210 is contained within the handle body 410 such that it moves forward in a single plane as it is advanced within the one or more grooves 115. In other words, the pin 210 does not have an up and down movement as it advances but rather it remains substantially within one plane. This type of movement by the pin 210 is created by disposing the ends of the pin 210 within longitudinal channels 220 that are formed in the handle body 410 on opposite sides of the inner tube 110. The channels 220 are aligned with one another so that they lie within one plane that also contains the pin 210. By placing the ends of the pin 210 within the channels 220, the channels 220 act as guide tracks in that they restrict and control the motion of the pin 210 after the unlocking of the second lever mechanism 170. In the retracted, locked position of the device 100, the ends of the pin 210 are disposed within the opposing slots near or at one end thereof and the pin 210 extends through the linear portion 117 of the groove 115. The pin 210 is thus limited to traveling within one plane since it is restricted to traveling within the linear channels 220. In order to accommodate the axial movement of the pin 210, the stylet 310 includes a slot 311 formed therethrough so as to permit the pin 210 to extend through the interior of the inner tube 110 to engage both channels 220, while still permitting the user to axially move the stylet 310 within and relative to the inner tube 110. The slot 311 allows axial motion of the pin which indirectly allows the inner tube 110 to move axially which allows ultimately the inner tube 110 and the outer cannula 120 to move together in an axial direction.

The operation of the device 100 will now be described. In the retracted position, the actuator device 150 and the second pivotable lever 170 are in the locked positions, whereby both the first biasing element 130 and the second biasing element 190 are in compressed states such that they store energy (FIG. 6). To actuate the device 100, the user presses, slides or otherwise manipulates the button 152 causing the pivoting of the post 154 and the claw 156 disengages from the annular flange 116. As soon as the claw 156 disengages, the first biasing element 130 releases its energy by applying a biasing force against the annular flange 116, which in turn causes the axial (longitudinal) movement of the inner tube 110 as well as the outer cannula 120 (FIG. 7). As previously mentioned, the distance that these two elements can axially travel is defined as distance x as illustrated in FIG. 6, namely the distance from the flange 126 to the handle body 410.

The first biasing element 130 is preferably a strong coil spring since this biasing element needs to generate a sufficient force that drives the inner and outer tubes 110, 120 into the tissue so as to shear the soft tissue to permit it to be collected as a result of the action of the snare 300.

Because the second pivotable lever 170 is connected to the inner tube 110, it will move along with the inner tube 110 when the actuator device 150 is activated. As the second pivotable lever 170 moves axially with the inner tube 110, the fixed pin 180 rides within the slot 173 toward the opposite end of the slot 173. Because the slot 173 is ramped or angled downward toward this opposite end, the relative movement of the fixed pin 180 within the slot 173 causes the second pivotable lever 170 to pivot upward about the pivot point between the lever 170 and the flange 113. As the lever 170 pivots upward, the claw 174 lifts up from its engagement with the member 200, thereby releasing the member 200 from its locked position (FIGS. 8-9). As soon as the member 200 is disengaged from the claw 174, the member 200 is free to move axially (longitudinally) along the inner tube 110 and the second biasing element 190 can release its energy. The second biasing element 190 applies a force against the member 200 in a direction toward the outer cannula 120. Preferably, the release of energy in the torque generating mechanism occurs after axial movement of the inner tube 110 is completed (FIGS. 8-9).

The pin 210 is placed adjacent the member 200 such that when the second biasing element 190 applies a force against the member 200, the force is also translated to the pin 210 causing the pin 210 to ride within the one or more grooves 115 that are formed in the inner tube 110. Initially, the pin 210 is disposed within the linear portion 117 of the groove 115 until the second pivotable lever 170 is actuated by lifting off from the member 200 resulting in the biasing force being applied against the pin 210. Because the ends of the pin 210 are constrained within the longitudinal channels 220, the pin 210 can only be advanced within one plane when it is "fired" forward by the biasing force of the second biasing element 190. Because the pin 210 is constrained to one plane, its forward advancement is translated into a rotational movement of the inner tube 110 due to the presence of the profiled helical portion 119 of the groove 115. As will be appreciated, the pin 210 advances within the channels 220 but at the same time, the pin 210 advances within the groove 115 from the linear portion 117 to the helical portion 119. The only way that the pin 210 can advance within the groove 115 and still remain within the channels 220 is if the inner tube 110 rotates to accommodate such movement of the pin 210. The helical nature of the portion 119 causes such rotational movement of the inner tube 110. It will be understood that the inner tube is axially fixed and therefore simply rotates in place as the torque action is imparted thereto. The torque generating mechanism can therefore be described as containing one component that is axially fixed but permitted to rotate, while the other component axially moves in the longitudinal direction.

It will be appreciated that the profile of the groove 115 can be varied and depending upon its precise characteristics, the movement of the inner tube 110 is controlled. For example, if it desired for the rotation of the inner tube 110 to be staged later in time, the length of the linear portion 117 can be increased and therefore, the pin 210 does not enter into the helical portion 119 as quickly as before and therefore, the rotation of the inner tube 110 is delayed.

Since the free end of the snare is fixed to the outer cannula 120, the result of the rotation of the inner tube 110 is that the coil of the snare tightens so that the cross-sectional area through the snare is approximately less than a third of the area when in the open configuration. It is also contemplated that any decrease, even a slight decrease, in the cross-sectional area of the snare will cause pressure on the biopsy piece. Therefore, the amount of rotation can be varied and there is no particular amount that is necessary for the proper functioning of the present invention.

With the tightening of the snare, there is a high probability that the biopsy piece will remain in the needle as the needle is removed. If the tightening of the snare does not immediately cause the biopsy piece to be cut, it will be significantly squeezed and/or notched, such that rearward motion of the needle, which causes rearward pressure on any biopsy piece proximal of the snare, will cause material proximal of the snare to detach from material that is distal of the snare.

The pin 210 advances forward until either (1) the pin 210 reaches the ends of the channels 220; (2) the pin 210 reaches the end of the helical portion 119; or (3) the pin 210 contacts the sleeve 160.

In the embodiment shown in FIGS. 1-9, the flange 113 does not move axially relative to the inner tube 110 although it does move axially relative to the handle body 410. The flange members 177, 179 permit the inner tube 110 to rotate within the flange 113 and in addition, the flange 113 does not rotate relative to the handle body 410 since the flange 113 is constrained by the interaction of the lever 170 and the pin 180.

The present construction according to the embodiment of FIG. 1 can therefore be thought of as a two stage mechanism in which the first stage is the firing of the actuator device 150 (first release of stored energy) to cause the sudden longitudinal advancement of the inner and outer tubes 110, 120 away from the handle body 410. This in turn causes the second pivotable lever 170 to disengage and there is a second firing of the second biasing element 190 which leads to the second stage where the inner tube 110 is rotated.

It will be appreciated that the first and second stages can occur simultaneously (some overlap) or the two stages can occur substantially one after the other. For example, the inner and outer tubes 110, 120 can be advanced by means of the first biasing element 130 to either their stopping point or close thereto at which time, the second pivotable lever 170 is disengaged and the second biasing element 190 releases its energy to cause a rotation of the inner tube 110 causing a tightening of the snare 300.

The operation of the snare 300 including the collection and removal of the soft tissue sample is preferably along the same lines as that which is disclosed in the patents disclosed hereinbefore.

To reset the device 100, a force is applied against the stop 128 in a direction toward the handle body 410. This motion causes the flange 116 to contact and slide underneath the surface of the claw 156 until the post 156 pivots and the locking surface engages the outer face of the inner flange 116, thereby locking the inner tube 110 and the outer cannula 120 in place. At the same time, the second pivotable lever 170 also resets itself and the claw 174 lockingly engages the member 200. In both of these positions, the biasing elements 130, 190 are placed again into a compressed state. The resetting of the pin and groove mechanism causes the pin 210 to rotate the inner tube 110 in a direction opposite to the direction that results from the actuation of the pin and groove mechanism when the claw 174 is released which in turn unwinds the snare 300 and frees the specimen for recovery.

One will appreciate that the speed of needle transit into a specimen with significant internal structure does not have to be excessive since the internal structure provides stability and supports the shearing of the specimen by the needle. However, needle transit into tissue must be excessive for tissues with moderate or minimal internal structure in order that an appropriate shearing and tissue cutting force is developed. Moreover, not only shearing but transit of the specimen into the needle is facilitated by specimens with significant internal structure. Tissue with minimal internal structure does not support transit of the specimen into the needle as well and requires the needle to "move over" the specimen in a rapid fashion to facilitate specimen acquisition. The present design is one in which the needle, with stylet in place, can be brought to a certain position and the coring needle can then be rapidly advanced beyond the fixed position of the stylet. Accordingly, the present spring loaded mechanism projects the needle over the stylet in a matter of microseconds.

In another aspect of the present invention and according to one exemplary embodiment, the rapid advancement of the needle to achieve appropriate shear/cutting forces and to facilitate specimen transit into the needle is accomplished by the spring loaded mechanism in which there is coordination between the rapid advancement of the needle over the shaft and activation of the winding down of the snarecoil. There are at least two possible designs to accomplish the aforementioned objective, namely (1) the first design requires that the rotation of the internal cannula is spring loaded and the projection of the needle beyond a certain distance over the stylet releases the spring loaded mechanism in such a way that the snare is activated only when the needle has projected a certain distance over the shaft; and (2) the second design uses one spring-loaded mechanism to achieve the forward energy of needle projection and snare activation. In this embodiment, a small pin radially projects from the stylet and engages a spiral (helical) groove (slot) cut into the inner cannula, thereby causing the inner cannula to rotate as the pin is dragged through groove as the needle is fired over the stylet. The pin and spiral groove mechanism can be located at various positions along the axial length of the needle that is either in the handle or more distally within the needle itself.

In another embodiment, a biopsy needle also includes two stages that are successive in nature and can at least partially overlap or can occur in series one after the other. At an end of the inner tube, a gear is provided. For example, the gear can be a plug type member which is inserted into an opening at the end. The gear is preferably a common type gear with a plurality of radial teeth extending therearound. The needle includes an outer cannula which includes a trigger tab or like. The tab can be an annular flange or it can be less than a complete circle. The tab includes a forward edge. The outer cannula is biased by a first biasing element that is operably coupled to an actuator which permits the user to selectively actuate the first biasing element. For example, the actuator can be a press button mechanism, slide mechanism or any number of other types of mechanisms that can cause the release of the compressed first biasing element so that it can apply a biasing force as its stored energy is released.

The actuation of the mechanism causes the outer cannula to be advanced forward. Since the inner tube is connected to the outer cannula at the snare, the inner tube is also advanced forward with the outer cannula. It will be appreciated that one or both of the inner tube and outer cannula can be provided with a flange at the respective proximal end so that the forward force is transmitted from the outer cannula to the inner tube through these flanges and not through the delicate snare.

The needle includes a second mechanism that is biased and serves as a positionable complementary drive gear that causes sufficient rotation of the inner tube to cause the snare to close slightly. A first lever or the like is provided and pivots about a point. After the first mechanism is actuated and the outer cannula advances to the end of its path of travel, the outer cannula strikes the first lever causing a pivoting movement thereof. The pivoting of the lever is translated into movement of a gear that is biased by a spring. More specifically, the gear is biased towards the inner tube such that the gear is brought into engagement with the gear. In other words, the gears mesh and the biasing force of the spring is translated into rotation of the inner tube which in turn causes the partial closing of the snare.

In this embodiment, one will appreciate that the second mechanism is only activated after the actuation of the first mechanism and even more particularly, the second mechanism is activated only when the outer cannula is at or near the end of its longitudinal travel. In other words, once the first stage (rapid advancement of the inner tube and outer cannula) is at or near completion, the second stage is initiated to cause the necessary rotation of the inner tube to close the snare and collect the tissue specimen therein.

It will be appreciated that there are a number of other different design constructions that accomplish the above intended function of coordinating the forward advancement of the inner tube and outer cannula with rotation of the inner tube to cause the snare to at least partially close. Thus, the present invention is broadly thought of as a needle that incorporates in one embodiment, a forward advancement mechanism (spring-loaded mechanism) for rapidly firing the inner tube and the outer cannula, wherein the inner tube includes a snarecoil to capture the tissue specimen. In another embodiment, the rapid firing of the inner tube and the outer cannula is coordinated with another mechanism so that forward axial motion of the inner tube/outer cannula is translated into rotation of the inner tube.

In sum, the pin and groove mechanism for rotating the snarecoil has been developed to eliminate the need for an operator to rotate a lever to actuate the snarecoil in applications where it is desirable to have a hand-held device that is spring-loaded and fired by pressing an activating button. Further, it coordinates the rapid axial projection of a needle with the requirement for a rotating movement to actuate the snarecoil. The pin and groove mechanism can achieve these requirements through a number of different embodiments. In these embodiments, the pin moves along the groove and this can be achieved by either translating a sleeve axially relative to a pin that does not move axially or vice versa translating the pin (can be attached to a tubular structure) relative to a grooved sleeve that does not move in an axial position. In each of these configurations, one component (either the sleeve or pin) does not rotate, while the other component does rotate. The component that rotates is connected to the internal snarecoil tubular member. The grooved sleeve is moved along an axial direction and a pin engages the sleeve by projecting into the groove in a radial fashion. In one embodiment, if the pin is fixed and does not rotate, axial movement of the sleeve causes the sleeve and any tube attached thereto (e.g., inner tube attached to snarecoil) to rotate. In the second embodiment, if the sleeve does not rotate, that is, it is fixed in a nonrotatable position when it is translated along an axial direction, the pin will rotate and any tubular member connected to the pin, such as the internal snarecoil cannula, will rotate as well.

FIG. 3 illustrates yet another aspect of the present invention. As previously mentioned, soft tissue specimens may not enter a needle as readily as specimens with more substantial internal structure because of issues of inadequate shearing/cutting and compromised specimen transit into the needle. One method of causing the specimens to more readily enter the needle is to create negative pressure (e.g., a vacuum condition) within the inner tube where the specimen is collected. Unfortunately, the existing needle constructions that have means for generating a negative pressure within the inner tube are very complex. For example, existing needle products include a cumbersome external vacuum device for generating the negative pressure.

As shown in FIG. 3, another way to generate a negative pressure internal to the needle is a means that takes advantage of the concept that when the needle is "thrown" forward over the stylet, the stylet is moving backward relative to the needle. As a result, the incorporation of a seal, such as a rubber O-ring or the like, between the stylet and the inner tube can generate a small but significant vacuum internal to the distal portion of the needle facilitating specimen transit into the needle. The vacuum is thus generated when the needle is "thrown" over the stylet and is cutting the tissue. For example, the needle can be "thrown" as a result of actuation of one of the aforementioned mechanisms.

The above feature of creating a negative pressure within the needle as it is fired can be the basis for a new biopsy technology. In one embodiment, a full core soft tissue needle projected forward and fired over a stylet that incorporates an air seal of some sort can generate enough internal negative pressure to not require the inclusion of a snarecoil in the needle to facilitate specimen recovery. Thus, in one embodiment, the snarecoil is removed and specimen recovery results from the application of a vacuum to the site.

In FIG. 3, the needle 100 is provided and includes inner tube 110 with the flange or the like 116 formed as a part thereof; the outer cannula 120 disposed around the inner tube 110; and the stylet 310. The stylet 310 has an outside diameter that is less than the diameter of the bore formed through the outer cannula 120 and therefore, there is a space or gap that is formed therebetween. In one embodiment, the flange 116 is an annular ring shapes member that extends outwardly from the inner tube 110. The outer cannula 120 also includes the flange or the like 126 that extends therearound.

A first seal element 500 is disposed between the flanges 116, 126. Any number of seal elements 500 can be used, including but not limited to a rubber washer like member, an O-ring, a lubricant, or other sealant. A second seal element 510 is disposed between the stylet 310 and the inner tube 110. As with the other embodiments, the second seal element 510 can be in the form of a rubber ring, such an O-ring or it can be some other type of seal member or material. This second seal element 510 that is disposed between the stylet 310 and the inner tube 110 acts as a positionably piston that generates the internal negative pressure in the needle, e.g., within the inner needle, to help draw the specimen by negative pressure into the inner tube 110. In other words, seal element 510 allows the inner tube 110 and outer cannula 120 to act as a composite tube which the stylet 310 works against to generate the vacuum.

According to this aspect of the present invention, the soft tissue needle incorporates inner tube and outer cannula which are fired or rapidly projected forward over the stylet that has some material (seal 510) disposed between the stylet and the inner tube that acts as an air seal. While the seal 510 can be in the form of an O-ring, it can also be in the formed of some type of medically compatible polymer that sits between the inner tube and the stylet and it does not result in significant friction and seals the forward space from atmospheric pressure. This concept can also be applied to needles having a cumbersome external vacuum source, such as a Mammotome design from Ethicon Industries. In this type of embodiment, the outer cannula is not thrown forward rapidly but moves slowly as the inner circulating cutting blade cores out a specimen. In such a design, a shaft with an air sealing component remains steadfast as the outer needle is slowly projected forward thereby producing as distal internal vacuum and not requiring the external vacuum device to generate the force to facilitate specimen transit and retention in the needle.

It will be appreciated that the above described vacuum generating means can be employed in both a snarecoil design and a standard biopsy needle that does not include a snarecoil.

Figure 11:
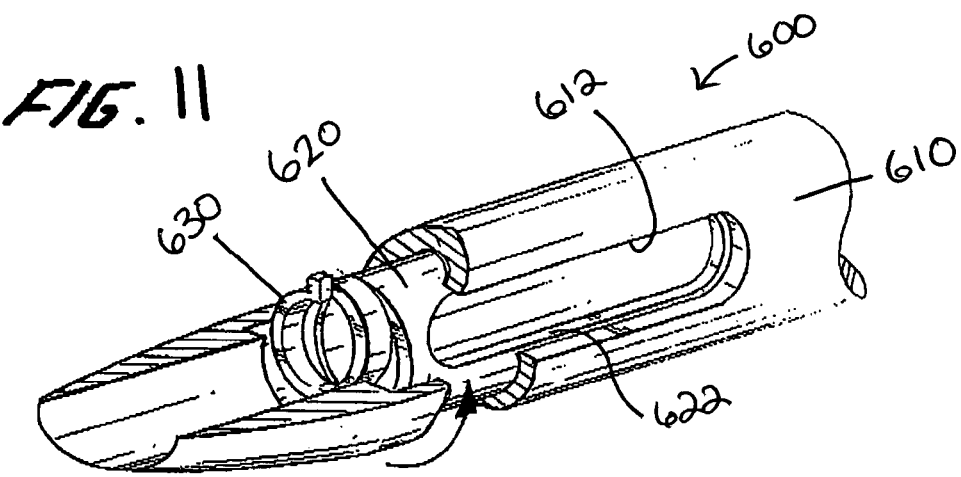
FIG. 11 is a perspective sectional view of a biopsy needle having an internal window feature according to a first embodiment.

FIG. 11 illustrates yet another aspect of the present invention. More specifically, a needle 600, such as the ones disclosed hereinbefore, includes an outer cannula 610 and an inner tube 620 that has or is connected to a snare 630 at a distal end thereof as previously described above and in the aforementioned patents. The outer cannula 610 includes a slot 612 that is formed therethrough to provide access into the interior of the outer cannula 610. For example, the slot 612 can have any number of different shapes and sizes so long as the slot 612 provides sufficient access into the interior of the outer cannula 610. The illustrated slot 612 is generally oblong shaped and is formed near the distal end of the outer cannula 610.

The inner tube 620 has a complementary slot 622 formed therein which is selectively axially aligned with slot 612 when the inner tube 622 is rotated within the outer cannula 610 to a position where the slots 612 and 622 at least partially overlap one another. The slot 622 extends completely through the inner tube 620 so as to permit the user to access the interior of the inner tube 620.

When the slots 612, 622 are aligned, a window is opened and permits the user to access the interior of the inner tube 620 from outside the outer cannula 610 by inserting an instrument through the side window into the interior of the inner tube 620 to access the specimen so that it can be removed through the window.

The inner tube 620 and the outer cannula 610 are arranged relative to the operable mechanisms of the needle such that when the inner tube 620 and outer cannula 610 are rapidly advanced forward the snarecoil 630 is actuated, the window defined by aligned slots 612, 622 remains closed. After the cutting/shearing action occurs, the snarecoil 630 is closed with the specimen being captured within the inner tube 620, the user then simply rotates the inner tube 620 so as to cause the inner slot 622 to become at least partially aligned with the outer slot 612, thereby opening the window and permitting easy removal of the specimen.

Figure 12:
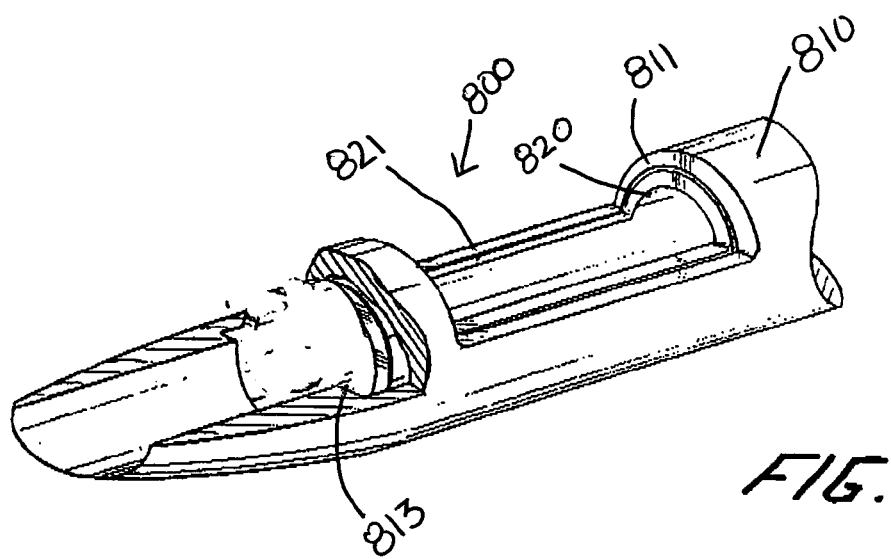
FIG. 12 is a perspective sectional view of a biopsy needle having an internal; window feature according to a second embodiment.

FIG. 12 is a perspective view of a simple biopsy needle 800 according to another embodiment in which the needle 800 does not include a snare feature but rather it is a simple biopsy needle incorporating one more of the above described features. More specifically, needle 800 includes an outer cannula 810 and an inner tube 820 that is disposed within the inside of the outer cannula 810 and more specifically, a distal end of the inner tube 820 rotatably sits on an annular shoulder formed 813 formed in the outer cannula 810. The outer cannula 810 includes a slot 811 that is formed therethrough to provide access into the interior of the outer cannula 810. For example, the slot 811 can have any number of different shapes and sizes so long as the slot 811 provides sufficient access into the interior of the outer cannula 810. The illustrated slot 811 is generally semi-circular shaped and is formed near the distal end of the outer cannula 810.

The inner tube 820 has a complementary slot 821 formed therein which is selectively axially aligned with slot 811 when the inner tube 820 is rotated within the outer cannula 810 to a position where the slots 811 and 821 at least partially overlap one another. The slot 821 extends completely through the inner tube 820 so as to permit the user to access the interior of the inner tube 820.

When the slots 811, 821 are aligned, a window is opened and permits the user to access the interior of the inner tube 820 from outside the outer cannula 810 by inserting an instrument through the side window into the interior of the inner tube 820 to access the specimen so that it can be removed through the window.

The inner tube 820 and the outer cannula 810 are arranged relative to the operable mechanisms of the needle such that the inner tube 820 and outer cannula 810 are rapidly advanced forward to cause a shearing (cutting) action to cut and collect the soft tissue sample therein. For example, at least the outer cannula 810 is biased such that when it is actuated, the outer cannula 810 and the inner tube 820 are rapidly advanced forward and the outer cannula 810 acts as a coring needle. As this occurs, the window defined by aligned slots 811, 821 remains closed so the specimen is collected in the distal tip of the outer cannula 810. After the cutting/shearing action occurs, the specimen is captured within the inner tube 820, the user then simply rotates the inner tube 820 so as to cause the inner slot 821 to become at least partially aligned with the outer slot 811, thereby opening the window and permitting easy removal of the specimen. It will be appreciated that the needle 800 is similar to the needle described and shown in FIGS. 4 and 5 with the exception that the needle 800 does not include a snare device at its end and therefore is simply a biopsy needle that can be fired forward to cause a cutting action of the tissue.

In another embodiment a biopsy needle according to another embodiment is shown and is similar to the previously needle in that it includes an internal vacuum feature; however, there is one main difference between the two needles, namely that the needle does not include a snare device. Needle includes a stylet and a cannula disposed around the stylet. The cannula has an opening formed at its distal end to accommodate the stylet so that the stylet can be advanced and retracted through the opening formed in the cannula. The position of the stylet is one where the needle is initially set and then brought into position relative to the site where tissue to be collected. The needle is then actuated to cause the cannula to be fired over the stylet and this rapid advancement generates the coring action when the cannula contacts the tissue.

A seal element is disposed between the stylet and the cannula. Any number of seal elements can be used, including but not limited to a rubber washer like member, an O-ring, a lubricant, or other sealant. The seal element acts as a positionable piston that generates the internal negative pressure in the needle, e.g., within the inner needle, to help draw the specimen by negative pressure into the cannula when the cannula is fired over the stylet. In other words, seal element allows the stylet and cannula to work against one another to generate the vacuum when the cannula is advanced over the stylet. This generation of negative pressure within the cannula is within the area where the specimen is received and collected and therefore, the negative pressure can help draw the specimen into the cannula. It will also be appreciated that the position of the sealing element can be changed relative to the initial position. For example, if the sealing element is moved backwards in the cannula, the negative pressure space is increased and this will lead to an increased negative pressure area assume the negative pressure is of sufficient strength.

It will also be understood that the various embodiments disclosed herein show different components of a working biopsy needle that can be combined with conventional components or with other components disclosed herein. For example, the components of FIGS. 11-12 can be combined with a snarecoil or they can be combined with other features disclosed herein or they can be combined with conventional components to form a working biopsy needle. Thus, FIGS. 11-12, the name a few, do not illustrate the working mechanisms of the handle assembly since conventional handle mechanisms are suitable.

In yet another embodiment that is similar to the embodiment of FIG. 1, a snarecoil type needle is provided which includes a flexible snarecoil that is made of a collapsible material that is incorporated into the needle. This snarecoil construction is constructed such that it decreases its diameter (winds down) as the inner tube moves forward. In this embodiment, the component (either the pin or groove) that is associated with the inner tube and the inner tube itself moves axially forward. In other words, this component is not steadfast in the axial direction but rather as the inner tube advances axially forward, e.g., as by activation of the rapid fire mechanism described above, either the pin or the helical groove that is part of the inner tube, advances axially and mates with the complementary component so as to impart a torquing action to the inner tube. In other words, the inner tube begins rotation as it axially moves forward and it continues such that the inner tube is simultaneously being axially driven forward and is rotating. In one embodiment, the component associated with the inner tube is one or more pins that protrude outwardly therefrom and ride with one or more complementary helical grooves formed in the housing of the handle assembly so as to cause rotation of the inner tube. The opposite arrangement is likewise suitable in that the component associated with the inner tube can be one or more helical slots that mates with one or more pins that are fixed to the housing of the handle assembly. Both of these embodiments result in axial firing and sufficient rotation of the inner tube to activate the snarecoil and unlike the other embodiments described herein, the torque component associated with the inner tube is characterized as being a moving part that axially moves within and relative to the housing of the handle assembly.

In yet another embodiment, the one or more helical slots formed in the inner tube are replaced with one or more outwardly projecting helical shaped ridges that mates with a pin as previously described. In one embodiment, the pin is driven by a biasing mechanism, such as the second biasing mechanism shown in FIG. 1, and contacts an edge of one helical ridge. As the pin is driven axially, the inner tube remains axially fixed but rotates due to the driving action of the pin against the helical projection as the pin is axially driven. This results in rotation of the inner tube and consequently results in activation of the snarecoil. If the inner tube has two complementary helical ridges, then two pins are provided and driven such that they engage the respective ridges causing rotation of the inner tube in one direction.

In a slightly modified form, the pin has a notch formed therein in the surface that faces and engages the helical projection. The notch has a complementary shape as the helical ridge such that the helical ridge is received in the notch so as to couple the two together, with the pin riding along the outer edge of the helical ridge. The driving of the pin along the outer edge of the helical projection is translated into rotation of the inner tube. As in the other embodiments, this needle construction is characterized by one component that travels axially, while the other component does not travel axially but rather remains axially steadfast or fixed. For example, the pin can be the component that is axially driven as by a mechanism shown in FIG. 1 and the inner tube has no substantial axial travel but rather merely rotates in place. Conversely, the pin can be the component that is axially fixed, while the helical ridge is the component that moves axially. In both of these arrangements, either the pin or the helical ridge can be formed as part of the inner tube.

In yet another embodiment, the present biasing mechanisms can be incorporated into a non-snarecoil rotating needle. In other words, this type of needle has a simple boring tube that has a biasing mechanism, such as the first biasing mechanism of FIG. 1, that causes the rapid axial advancement of the boring tube due to the release of energy that is stored in the first biasing element against the flange of the boring tube. The needle also has a rotating mechanism, such as the pin and groove arrangement of FIG. 1, that causes the rotation of the boring tube either concurrently with the axial advancement of the boring tube or after the boring tube has reached its end of axial travel. In this embodiment, there is no inner tube and no automatic active capture mechanism that results in actuation of a snarecoil since there is no snarecoil. As with the other previous embodiments, the rotating mechanism of the boring tube preferably includes one component, such as a pin or helical slot, that moves axially and another component, such as a helical slot or pin, that is axially steadfast. Either pin or the helical slot or even a helical ridge as described above can be associated with the boring tube, while the other complementary component is formed as part of the housing of the handle assembly.

In addition, it will be appreciated that the window feature shown in FIGS. 11 and 12 and the vacuum feature shown in FIG. 3 can be incorporated into any of the needle embodiments disclosed herein. For example, the window feature can be used in both snarecoil type needles and non-snarecoil type needles and can be used in needles that incorporate one or more of the mechanisms that either drive the needle axially forward or cause rotation of a part of the needle. Similarly, the window feature can be combined with the vacuum feature or the needle can include only one of these features and the vacuum feature similarly can be used in any of the above embodiments, including both snarecoil type needles and non-snarecoil type needles.

Figure 14:
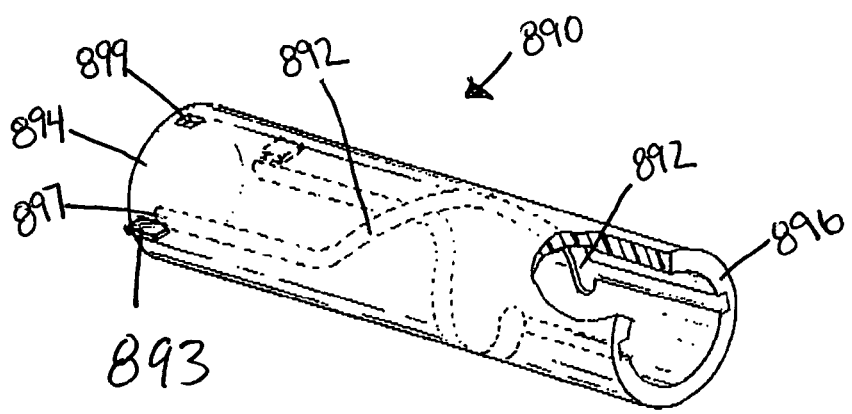
FIG. 14 is perspective view, partially in cross-section, of the movable helical sleeve of FIG. 13.
Figure 13:
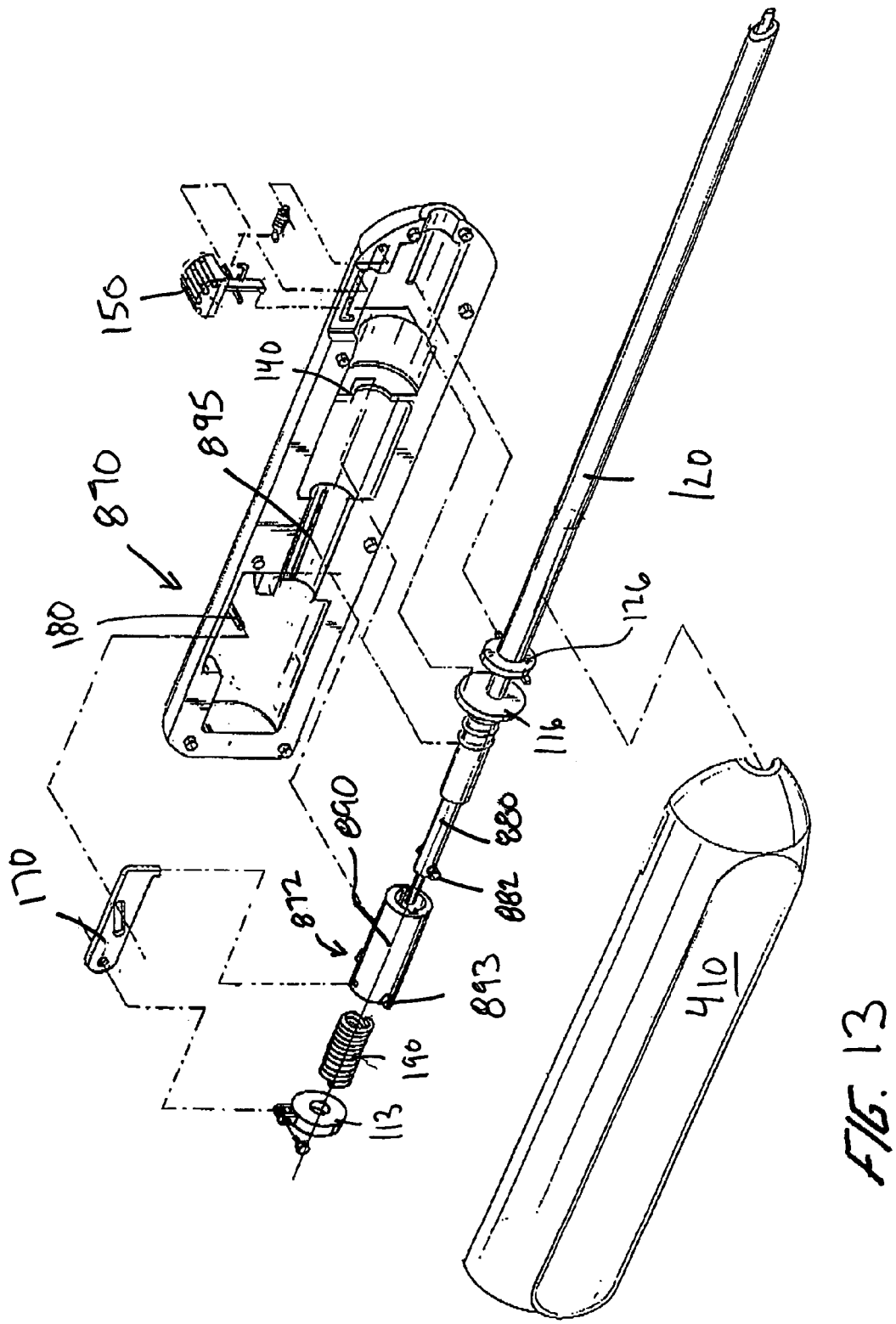
FIG. 13 is biopsy needle according to a second embodiment having an axially movable helical sleeve.

FIGS. 13-14 illustrates a biopsy needle 870 according to another embodiment. The needle 870 is similar to needle 100 and therefore like elements are numbered alike. In both these embodiment and as previously described, the torque generating mechanism that is employed to rotate the inner tube, which remains substantially fixed in the axial direction, is one in which one component is axially fixed, while the other is axially translated so as to cause rotation of the inner tube.

In FIGS. 13-14, a torque generating mechanism 872 is provided and includes the second pivotable lever 170 and the second biasing element 190; however, the linear channels 220 and the ring shaped member 200 are eliminated. In this embodiment, an inner tube 880 is provided and is similar to tube 110 with the exception that the helical groove 115 is eliminated and replaced with one or more projections (bosses) 882 that extend outwardly from an outer surface of the inner tube 880, preferably at a right angle thereto. If two projections 882 are provided, they are preferably orientated 180 degrees apart. In this embodiment, the mechanism 872 includes an axially driven helical sleeve 890 that is disposed about the inner tube 872 and includes one or more helical grooves or slots 892 formed therein, similar to grooves 115 in FIG. 1. If there are two projections 882, then there are two slots 892. The sleeve 890 also includes one or more, preferably two, guide fins or projections 893 that ride within guide channels 895 formed in the inner housing body 410 so as to prevent rotation of the sleeve 890 as the sleeve 890 travels axially within the housing.

The sleeve 890 is contained in the housing body 410 and is permitted a degree of longitudinal axial travel therein. The sleeve 890 includes a proximal end 894 that has an opening or slot 899 formed thereat with a distal end 896 being disposed near but spaced from the flange 116. The helical slot 892 has an initial linear portion 897 into which the projection 882 is disposed and will travel in as the inner tube 880 moves axially in the first stage due to the firing of the first biasing element 130 and movement of the outer tube 120 similar to FIG. 1. The slot 899 of the sleeve 890 is initially engaged and locked by the claw 174 of lever 170. As in FIG. 1, after a predetermined distance of axial travel, the lever 170 disengages from the sleeve 890, thereby causing the second biasing element 190 to release its energy against the flange 894 to cause axial movement of the sleeve 890 about the inner tube 880 which does not move axially any more since the first stage is completed. It will be appreciated that once the sleeve 890 is fired over the axially stationary inner tube 880, the engagement between the projections 882 and the helical slots 892 causes rotation of the inner tube 880 and thereby causes activation of the snare. Once again, this embodiment shows an automatic active capture mechanism that is automatically fired after actuation of the first stage (longitudinal firing of the inner tube 880 and the outer cannula 120) and at a predetermined time relative to the completion of the first stage.

After firing, the degree of axial travel of the sleeve 890 can be restricted by a stop or the like, such as an object formed as part of the housing 410 and in any event, the travel of the sleeve 890 will be limited by the presence of the flange 116. Once again, the guide channels 895 prevent rotation of the axially advancing sleeve 890.

Now referring to FIG. 15 in which a needle 900 according to another embodiment is illustrated. The needle 900 shares a number of features in common with the needles previously described herein. More specifically, the needle 900 contains a torque generating mechanism for imparting a torque action to an inner tube 910 that is part of the needle 900. The needle 900 is of the snarecoil type in that inner tube 910 is operatively connected to the snarecoil such that when the inner tube 910 is rotated in one direction, the snarecoil winds down so as to capture the tissue specimen as previously described. It will be understood that only the torque generating mechanism of the needle 900 is shown in the figure and it will be appreciated that the inner tube 910 is of the type that is axially advanced, either manually or automatically, in order to insert the needle into the patient for capturing the tissue specimen. In one embodiment, the inner tube 910 is advanced as part of a biasing mechanism such as the first biasing mechanism of FIG. 1 which causes the rapid axially advancement of the inner tube, as well as an outer cannula, toward the patient so as to project the needle 900 into the target site.

FIG. 15 shows a proximal end 912 of the inner tube 910 which includes a first beveled section 914 and a second beveled section 916 that meet at a point since the two sections 914, 916 are beveled in opposite directions. The inner tube 910 also has a boss 920 that is formed at and defines the proximal end 912 of the inner tube 910. In the illustrated embodiment, the boss 920 has a generally cylindrical shape; however, it can be in any number of other shapes so long as the boss 920 includes a longitudinal channel or notch 922 formed therein and extending the length of the boss 920 and being open at one end thereof.

The torque generating mechanism of the needle 900 is formed of a rotating knob 930 that is at least partially hollow, a torque dowel 940, and an biased lever 950 that moves between a locked position in which the lever 950 prevents the inner tube 910 from rotating independently from the rotating knob 930. The rotating knob 930 is received through an opening 924 that is formed in the housing 901 of a handle body 902 of the needle 900 such that a first section of the knob 930 is disposed on an interior side of the body 902, while a second side is disposed on an exterior side of the body 902. As previously mentioned, the knob 930 is at least partially hollow in that at the end of the knob 930 that is located on the interior of the housing wall is hollow so as to define a compartment 931 for receiving the boss 920. In the illustrated embodiment, the knob 930 has a cylindrical shape; however, this shape is merely exemplary and the knob 930 can have any number of other shapes so long as the compartment 931 has a complementary shape to receive the boss 920.

Within the compartment 931 and formed as part of the knob 930 is a longitudinal rail 925 that extends a substantial length of the compartment 931 and has a shape that is complementary to the channel or notch 922 formed in the boss 920. It will be appreciated that the inner tube 910 is thus located and permitted to travel axially within and relative to the knob 930 by inserting the rail 925 into the channel 922, thereby permitting at least the boss 920 to travel axially within the compartment 931 during operation of the needle 900 as described below. It will further be appreciated that the rail 925 acts as a locator or key and prevents the inner tube 910, more particularly, the boss 920 thereof, to rotate independently from the knob 930. Thus, at least when the rail 925 is engaged in the channel 922, any rotation of the knob 930 is directly imparted to the inner tube 910.

The torque dowel 940 can come in any number of shapes and sizes beyond the generally cylindrically shaped one shown in the figure. The illustrated torque dowel 940 has a first end 942 that faces the compartment 931 and the inner tube 910 and an opposing second end 944 that faces the housing of the handle body 902. The torque dowel 940 is formed of a material that is able to store a torque as stored energy. In other words, the torque dowel 940 is formed of a material that can be twisted (torqued) to store the energy and then upon release of the dowel 940, the dowel 940 will twist back to its original state, thereby releasing the stored energy as a torque action. The first end 942 of the dowel is directly coupled to the knob 930 by being attached to a section thereof, such as the rail 924 or a wall of the knob 930. In contrast, the second end 944 of the knob 940 is not directly attached to the knob 930 but rather is coupled to the stationary housing of the handle body 902. As a result of this arrangement, when the user turns the knob 930, the first end 942 of the dowel 940 is rotated and the dowel begins to twist since the second end 944 is not connected to the rotating knob 930 but rather is fixed to the housing body 902 itself. Since one end is fixed to a stationary fixed point and the other end is attached to a rotating body, the net result is that the dowel 940 begins to twist (torque) and store energy (store torque). The complete operation of the needle 900 is described below.

The lever 950 is positionable between a closed position and an open position and include a base 952 that is attached to the knob 930 and a pivotable elongated lever 954 that is pivotally attached to the base 952. The lever 954 has a claw 956 formed at one end that is constructed to engage the inner tube 910 for holding the inner tube 910 so as to prevent the inner tube 910 from easily falling out of the compartment 931. When the boss 920 is inserted into the compartment 931 and is in the fully locked position, the claw 956 engages and outer surface of the inner tube 910 prior to the formation of the two beveled ends. As the inner tube 910 is driven axially, either manually or by means of an automated mechanism, the claw 956 lifts and disengages from the beveled surfaces of the inner tube, thereby causing the free axially movement of the inner tube 910. The elongated lever 954 is normally biased downwardly toward the inner tube 910 so as to urge the claw 956 against the inner tube 910 to hold the inner tube 910 in place.

In operation, the user first rotates the knob 930 so as to impart and store a torque energy force in the dowel 940 as described above. After sufficiently, rotating the knob 930 in a first direction and storing energy in the torque dowel 940, the user then axially drives at least the inner tube 910 axially away from the handle body 902 and towards a tissue site for collecting the tissue specimen. The inner tube 910 can be driven either manually or automatically. As the inner tube 910 is fired and driven axially, the boss 920 travels about the rail 924 but does not completely disengage from the rail 924 when the inner tube 910 reaches its end of axial travel. In other words, during the axial firing of the inner tube 910, the boss 920 remains in the compartment 931 and simply travels from one end of the compartment 931 to the other end of the compartment 931. The lever 950 disengages from the inner tube 910 is fired axially forward.

Next, after the inner tube 910 reaches its end of axial travel, the user releases the stored energy by simply releasing the knob 930. After releasing the knob 930, the energy stored in the dowel 940 is released by a torque action (twisting) in the opposite second direction until the dowel 940 is returned to its original rest condition. This release of energy is translated directing to rotation of the knob 930 in this second direction and since the inner tube 910 is coupled to the knob 930, the rotation of the knob 930 is directly translated to rotation of the inner tube 910. In other words, the release of stored energy is in effect an unwinding of the knob 930 and the dowel 940. This rotation causes the activation of the snarecoil as in the other embodiments.

In one embodiment, the second end 944 of the dowel 940 can be attached to the housing body 902 in any number of different ways. For example, the second end 944 can be securely attached to a spoke or finger 960 that is part of the housing body 902 and extends into the opening that receives the knob 930. The finger 960 is accommodated in the knob 930 by passing through a slot 962 formed around a circumference of the knob 930. The slot thus permits rotation of the knob 930 relative to the finger since the finger 960 is stationary and fixed relative to the movable knob 930. As the knob 930 is rotated, the fixed finger 960 moves within the slot 962 from one end toward the other end and once the energy is released by letting go of the knob 930, the finger 960 travels back in the opposite direction within the slot 962.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof. In addition, the features of the different claims set forth below may be combined in various ways in further accordance with the present invention.

What is claimed is:

1. A biopsy needle for collecting a tissue specimen, the needle including an inner tube with a snarecoil operatively connected at a distal end thereof, an outer cannula, a stylet and a handle assembly that includes a biasing mechanism that permits a user to selectively actuate the biopsy needle so that the outer cannula and the inner tube are rapidly advanced over the stylet and beyond a distal end thereof to provide a shearing action of the tissue specimen, wherein the biasing mechanism includes features that provide coordination between the rapid advancement of the outer cannula and the inner tube over the stylet and activation of a winding down of the snarecoil.

2. The needle of claim 1, wherein the features include a pin and a profiled groove arrangement wherein forward axial movement of the outer cannula and inner tube is translated into rotation of the inner tube relative to the outer cannula which causes the snarecoil to at least partially close.

3. The needle of claim 2, wherein the inner tube has the groove formed therein and the pin extends therein such that as the pin travels within the groove as the outer cannula and inner tube advance due to ends of the pin being fixedly coupled to side walls of the handle assembly such that the pin travels axially within one plane.

4. The needle of claim 1, wherein the biasing mechanism includes a torque mechanism that imparts a selective and controlled torque action in the inner tube relative to the outer cannula resulting in activation of a winding down of the snarecoil.

5. The needle of claim 1, wherein the biasing mechanism includes a first biasing mechanism to provide the selective sudden advancement of the inner tube and the outer cannula when a first actuator is activated by a user, the first biasing mechanism including a first biasing element that in an energy storing position is compressed between a body member of the handle assembly and an outer flange associated with the inner tube.

6. The needle of claim 5, wherein a proximal end of the outer tube terminates in a flange that abuts the flange of the inner tube, wherein activation of the first biasing mechanism results in release of the first biasing element causing an axial force to be applied against the flange of the inner tube, whereby the inner tube and the outer cannula are driven axially in tandem a prescribed distance until the flange of the outer cannula contacts a stop surface of the handle assembly.

7. The needle of claim 5, wherein the first biasing mechanism includes a first actuator operatively coupled to pivoting links that terminate in a claw at one end that engages the flange of the inner tube in the energy storing position so as to restrict axial movement of the inner tube and maintain the first biasing element in a compressed state.

8. The needle of claim 1, wherein during a rapid advancement stage, the inner tube and the outer cannula move in tandem and substantially free of rotation relative to one another.

9. The needle of claim 5, wherein the biasing mechanism includes a second biasing mechanism that automatically actuates at a predetermined point when the inner tube and outer cannula are axially advancing after activation of the first biasing mechanism, the inner tube including one of a drive pin and a groove and a housing of the handle assembly including the other of the drive pin and groove such that as the inner tube and the outer cannula axially moves, the drive pin travels within the groove that is helically shaped so as to impart a rotation to the inner tube relative to the outer cannula as the drive pin travels within the helical groove.

10. The needle of claim 9, wherein the second biasing mechanism includes:

a second pivoting member that is pivotably coupled at a first end to a proximal end of the inner tube, with a second end including a claw, the second pivoting member includes a cam slot that receives a fixed pin that is fixed to the housing of the handle assembly such that as the inner tube and outer cannula move axially, the fixed pin travels within the cam slot causing a lifting of the second end;

a retainer ring disposed about the inner tube and being engaged by the claw when the second biasing mechanism is in an energy storing position;

a second biasing element disposed between the proximal end of the inner tube and the retainer ring and in a compressed state in the energy storing position; and wherein when the second biasing mechanism is activated, the claw lifts off the retainer ring, thereby releasing the retainer ring and the second biasing element.

11. The needle of claim 10, wherein the drive pin contacts the retainer ring such that release of the retainer ring drives the drive pin within guide grooves that are formed in the handle assembly and contain the drive pin in a single plane, the stylet having an opening formed therethrough to accommodate the drive pin, wherein planar advancement of the drive pin in the guide slots and advancement of the drive pin in the helical groove is translated into rotation of the inner tube relative to the outer cannula.

12. The needle of claim 9, wherein the predetermined point occurs prior to the inner tube and the outer cannula reaching the end of their axial travel such that rotation is imparted to the inner tube as it axially advances.

13. The needle of claim 9, wherein the predetermined point occurs after the inner tube and the outer cannula reach ends of their axial travel.

14. A biopsy needle for collecting a tissue specimen, the needle including an inner tube with a snarecoil operatively connected at a distal end thereof, an outer cannula, a stylet and a handle assembly that includes a biasing mechanism that permits a user to selectively actuate the biopsy needle so that the outer cannula and the inner tube are rapidly advanced over the stylet and beyond a distal end thereof to provide a shearing action of the tissue specimen and further including means for generating negative pressure within the needle for causing the specimen to more readily enter the needle, the means including a first seal and a second seal, the first seal being disposed between the stylet and the inner tube that generates a vacuum within a distal portion of the needle during axial travel of the inner tube and the outer cannula facilitating specimen transit into the needle, the second seal being disposed between the outer cannula and the inner tube.

15. A biopsy needle for collecting a tissue specimen, the needle including an inner tube with a snarecoil operatively connected at a distal end thereof, an outer cannula, a stylet and a handle assembly that includes a biasing mechanism that permits a user to selectively actuate the biopsy needle so that the outer cannula and the inner tube are rapidly advanced over the stylet and beyond a distal end thereof to provide a shearing action of the tissue specimen, wherein the outer cannula has a first window formed therein and the inner tube has a second window which is selectively aligned with the first window when the inner tube is rotated within the outer cannula to a position where the windows at least partially overlap one another after the snarecoil is tightened to permit access to the specimen collected in the needle.

16. A biopsy needle for collecting a tissue specimen, the needle including an inner tube with a snarecoil operatively connected at a distal end thereof, an outer cannula, a stylet and a handle assembly that includes an actuatable axial drive mechanism for rapidly driving the inner tube and the outer cannula, in a longitudinal axial direction, over the stylet to a position where the inner tube and the outer cannula are advanced beyond a distal end of the stylet to provide a shearing action of the tissue specimen, and a torque generating mechanism associated at least in part with the inner tube that is actuatable to translate a torque to the inner tube relative to the outer cannula resulting in activation of a winding down of the snarecoil, the actuation of drive mechanism and the torque generating mechanism being coordinated with one another.

17. The needle of claim 16, further including:
means for generating negative pressure within the needle for causing the specimen to more readily enter the needle, the means including a first seal and a second seal, the first seal disposed between the stylet and the inner tube that generates a vacuum within a distal portion of the needle during axial travel of the inner tube and the outer cannula facilitating specimen transit into the needle, the second seal being disposed between the outer cannula and the inner tube.

18. The needle of claim 16, wherein the outer cannula has a first window formed therein and the inner tube has a second window which is selectively aligned with the first window when the inner tube is rotated within the outer cannula to a position where the windows at least partially overlap one another after the snarecoil is tightened to permit access to the specimen collected in the needle.

19. The needle of claim 16, wherein the torque generating mechanism includes a first torque feature that is associated with a proximal end of the inner tube and is axially movable with inner tube as the inner tube is axially moved in response to actuation of the axial drive mechanism, the first torque feature mating with a second torque feature that is associated with a housing of the handle assembly and is fixed in the axial direction relative to the inner tube, wherein the first torque feature comprises one of a pin and a helical slot and the second torque feature comprises one of a helical slot and a pin, wherein engagement of the first and second torque features concurrently with axial advancement of the inner tube imparts rotation to the inner tube, thereby actuating the snarecoil.

20. A biopsy needle for collecting a tissue specimen, the needle including an inner tube with a snarecoil operatively connected at a distal end thereof, an outer cannula and a handle assembly that includes a torque generating mechanism associated at least in part with the inner tube that is actuatable to translate a torque to the inner tube relative to the outer cannula resulting in activation of a winding down of the snarecoil and capture of the specimen, wherein the torque generating mechanism includes a drive pin and a profiled groove arrangement, wherein forward axial movement of the outer cannula and inner tube is translated into rotation of the inner tube relative to the outer cannula which causes the snarecoil to at least partially close.

21. The needle of claim 20, wherein one of the drive pin and the profiled groove is associated with a proximal end section of the inner tube and the other of the profiled groove and the drive pin is associated with the handle assembly as is free of association with the inner tube.

22. The needle of claim 21, wherein the one of the drive pin and the inner tube that has the profiled groove travels in an axial direction, while the other of the drive pin and the inner tube remains substantially axially fixed.

23. The needle of claim 20, wherein the inner tube has the profiled groove formed therein in a shape of a helix and the drive pin extends therethrough with ends of the drive pin traveling within axial guide grooves formed in side walls of the handle assembly such that the drive pin travels axially within one plane such that axial travel of the drive pin in the guide grooves is translated into rotation of the inner tube relative to the outer cannula.

24. The needle of claim 20, further including an axial drive mechanism to selectively and rapidly advance the inner tube and the outer cannula over the stylet and beyond a distal end thereof to provide a shearing action of the tissue specimen.

25. The needle of claim 24, wherein the axial drive mechanism includes a first biasing mechanism including a first biasing element that in an energy storing position is compressed between a body member of the handle assembly and an outer flange associated with the inner tube and wherein a proximal end of the outer tube terminates in a flange that abuts the flange of the inner tube, wherein activation of the axial drive mechanism results in release of the first biasing element causing an axial force to be applied against the flange of the inner tube, whereby the inner tube and the outer cannula are driven axially in tandem a prescribed distance until the flange of the outer cannula contacts a stop surface of the handle assembly.

26. The needle of claim 25, wherein the axial drive mechanism includes a first actuator operatively coupled to pivoting links that terminate in a claw at one end that engages the flange of the inner tube in the energy storing position so as to restrict axial movement of the inner tube and maintain the first biasing element in a compressed state.

27. The needle of claim 24, wherein during a rapid advancement stage, the inner tube and the outer cannula move in tandem and substantially free of rotation relative to one another.

28. The needle of claim 25, wherein the torque generating mechanism includes a second biasing mechanism that automatically actuates at a predetermined point when the inner tube and outer cannula are axially advancing after activation of the axial drive mechanism, the inner tube including one of a drive pin and a groove and a housing of the handle assembly including the other of the drive pin and groove such that as the inner tube and the outer cannula axially moves, the drive pin travels within the groove that is helically shaped so as to impart a rotation to the inner tube relative to the outer cannula as the drive pin travels within the helical groove.

29. The needle of claim 28, wherein the torque generating mechanism includes:
a second pivoting member that is pivotably coupled at a first end to a proximal end of the inner tube, with a second end including a claw, the second pivoting member includes a cam slot that receives a fixed pin that is fixed to the housing of the handle assembly such that as the inner tube and outer cannula move axially, the fixed pin travels within the cam surface causing a lifting of the second end;
a retainer ring disposed about the inner tube and being engaged by the claw when the second biasing mechanism is in an energy storing position;
a second biasing element disposed between the proximal end of the inner tube and the retainer ring and in a compressed state in the energy storing position; and wherein when the second biasing mechanism is activated, the claw lifts off the retainer ring, thereby releasing the retainer ring and the second biasing element.

30. The needle of claim 29, wherein the drive pin contacts the retainer ring such that release of the retainer ring drives the drive pin within guide grooves that are formed in the handle assembly and contain the drive pin in a single plane, the stylet having an opening formed therethrough to accommodate the drive pin, wherein planar advancement of the drive pin in the guide slots and advancement of the drive pin in the helical groove is translated into rotation of the inner tube relative to the outer cannula.

31. The needle of claim 28, wherein the second biasing mechanism releases stored energy to cause rotation of the inner tube after the inner tube completes its longitudinal axial movement such that the inner tube rotates and remains substantially axially steadfast during actuation of the second biasing mechanism.

32. A needle for collecting a specimen comprising:
a stylet;
an inner tube that slidably receives the stylet through a bore formed therethrough;
an outer cannula disposed about the inner tube, wherein during activation of the needle, the inner tube and the outer cannula travel axially over and beyond a distal end of the stylet; and
means for generating negative pressure within the needle for causing the specimen to more readily enter the needle, the means including a first seal and a second seal, the first seal being disposed between the stylet and the inner tube that generates a vacuum within a distal portion of the needle during axial travel of the inner tube and the outer cannula facilitating specimen transit into the needle, the second seal being disposed between the outer cannula and the inner tube.

33. The needle of claim 32, wherein each of the first and second seals comprises an O-ring.

34. A biopsy needle for collecting a tissue specimen, the needle including an inner tube with a snarecoil operatively connected at a distal end thereof, an outer cannula and a handle assembly that includes a torque generating mechanism associated with the inner tube that is actuatable to translate a torque to the inner tube relative to the outer cannula resulting in activation of a winding down of the snarecoil, wherein the outer cannula has a first window formed therein and the inner tube has a second window which is selectively aligned with the first window when the inner tube is rotated within the outer cannula to a position where the windows at least partially overlap one another after the snarecoil is tightened to permit access to the specimen collected in the needle.

35. The needle of claim 34, wherein the windows are offset from one another prior to actuation of the torque generating mechanism.

36. A biopsy needle for collecting a tissue specimen comprising a boring tube and a biasing mechanism operatively connected to the boring tube, the biasing mechanism permitting a user to selectively actuate the needle to cause the boring tube to rapidly advance axially over a stylet and beyond a distal end thereof to provide a shearing action of the tissue specimen as a result of a distal end of the boring tube being driven into the tissue specimen, the needle further including means for generating negative pressure within the needle for causing the specimen to be drawn into the needle, the means including a first seal and a second seal, the first seal disposed between the stylet and the boring tube, the second seal being disposed between the boring tube and another element of the needle, the first and second seals generating a vacuum within the boring tube as the boring tube is axially advanced over the stylet.

37. A biopsy needle for collecting a tissue specimen comprising a stylet, an inner tube disposed about the stylet the inner tube having a snarecoil at a distal end thereof, an outer cannula disposed about the inner tube and a handle assembly, wherein the snarecoil is operatively connected to the outer cannula and the outer cannula has a first window formed therein and the inner tube has a second window which is selectively aligned with the first window when the inner tube is rotated within the outer cannula to a position where the windows at least partially overlap one another to permit retrieval and removal of the specimen collected in the inner tube as a result of activation of the snarecoil.

* * * * *